United States Patent
Seth et al.

Patent Number: 5,928,944
Date of Patent: Jul. 27, 1999

[54] METHOD OF ADENOVIRAL-MEDICATED CELL TRANSFECTION

[75] Inventors: Prem Seth, North Potomac; Ronald G. Crystal, Potomac; Melissa Rosenfeld, Bethesda, all of Md.; Kunihiko Yoshimura, Tokyo, Japan

[73] Assignee: The United States of America as represented by the Department of Health and Human Services, Washington, D.C.

[21] Appl. No.: 08/191,669

[22] Filed: Feb. 4, 1994

[51] Int. Cl.⁶ .......................... A61K 48/00; A61K 9/127; A01N 63/00; C12N 5/00
[52] U.S. Cl. .................. 435/375; 435/172.1; 435/172.3; 424/93.1; 424/93.2; 424/450; 514/44; 935/55; 935/56; 935/57
[58] Field of Search .................. 435/240.2, 320.1, 435/172.3, 172.1, 375; 424/450, 93.21, 93.1, 93.2; 514/44; 935/55–57; 800/2

[56] References Cited

U.S. PATENT DOCUMENTS

| | | | |
|---|---|---|---|
| 4,789,633 | 12/1988 | Huang et al. | 435/172.2 |
| 4,897,355 | 1/1990 | Eppstein et al. | 435/172.3 |
| 5,043,164 | 8/1991 | Huang et al. | 424/423 |
| 5,049,386 | 9/1991 | Eppstein et al. | 424/427 |
| 5,264,618 | 11/1993 | Felgner et al. | 560/224 |
| 5,283,185 | 2/1994 | Epand et al. | 435/172.3 |
| 5,334,761 | 8/1994 | Gebeyehu et al. | 564/197 |
| 5,547,932 | 8/1996 | Curiel et al. | 435/65 |
| 5,635,680 | 6/1997 | Naftilan et al. | 435/172.3 |

FOREIGN PATENT DOCUMENTS

| | | |
|---|---|---|
| WO 90/11092 | 10/1990 | WIPO . |
| WO 91/17424 | 11/1991 | WIPO . |
| WO 93/03709 | 3/1993 | WIPO . |
| WO 93/05162 | 3/1993 | WIPO . |
| WO 93/14778 | 8/1993 | WIPO . |

OTHER PUBLICATIONS

Loke et al., Proc. Natl. Acad. Sci. USA, 86:3474–3478 (1989).

Zatloukal et al., Verh. Dtsch. Ges. Path., 78:171–176 (1994).

Legendre et al., Pharmaceutical Research, 9(10): 1235–1242 (1992).

Akhtar et al., J. Pharm. Pharmacol. Suppl., 43:12, abstract No. 23P (1991).

Yakubov et al., Proc. Natl. Acad. Sci USA, 86:6454–6458 (1989).

(List continued on next page.)

*Primary Examiner*—Bruce R. Campell
*Attorney, Agent, or Firm*—Leydig, Voit & Mayer, Ltd.

[57] ABSTRACT

The present invention provides an adenoviral-mediated method of transfection with nucleic acids which can be augmented through incubation of the nucleic acids with cationic agents. Specifically, the present inventive method of introducing a nucleic acid into a eukaryotic cell comprises contacting the cell with, in any order or simultaneously, the nucleic acid and an adenovirus, wherein the nucleic acid is not bound to any molecule capable of effecting its entry into the cell. The cell is preferably additionally contacted with a cationic agent, such as a monocationic or polycationic liposome, such that the nucleic acid is not bound to any molecule capable of effecting its entry into the cell other than, optionally, the cationic agent.

50 Claims, 13 Drawing Sheets

OTHER PUBLICATIONS

Askari, "DNA/Protein Complexes Delivered in Conjunction with Adenovirus Generate High–Efficiency in vitro Transfection: A Powerful Transfection Reagent with Potential Broad Applications", *Hepatology*, 18(6), 1537–9 (Dec. 1993).

Blakely et al., "Vaccinia–T7 RNA Polymerase Expression System: Evaluation for the Expression Cloning of Plasma Membrane Transporters", *Anal. Biochem.*, 194(2), 302–8 (1991).

Blumenthal et al., "pH–Dependent Lysis of Liposomes by Adenovirus", *Biochemistry*, 25, 2231–2237 (1986).

Carrasco, "Modifidation of Membrane Permeability Induced by Animal Viruses Early in Infection," *Virology*, 113, 523–629 (1981).

Carrasco et al., "Modification of Membrane Permeability in Vaccinia Virus–Infected Cells", *Virology*, 117, 62–69 (1982).

Cotten et al., "High–Efficiency Receptor–Mediated Delivery of Small and Large 48 Kilobase Gene Constructs Using the Endosome–Disruption Activity of Defective or Chemically Inactivated Adenovirus Particles", *Proc. Natl. Acad. Sci.*, 89, 6094–6098 (1992).

Cotten et al., "Chicken Adenovirus (CELO Virus) Particles Augment Receptor–Mediated DNA Delivery to Mammalian Cells and Yield Exceptional Levels of Stable Transformants", *J. Virol.*, 67, 3777–3785 (1993).

Cotten et al., "Receptor–Mediated Transport of DNA into Eukaryotic Cells", *Methods in Enzymol.*, 217, 618–654 (1993).

Curiel et al., "Adenovirus Enhancement of Transferrin–olylysine–Mediated Gene Delivery", *Proc. Natl. Acad. Sci.*, 88, 8850–8854 (1991).

Curiel et al., "High–Efficiency Gene Transfer Mediated by Adenovirus Coupled to DNA–Polylysine Complexes", *Hum. Gene Therapy*, 3, 147–154 (1992).

Cussenot et al., "Immortalization of Human Adult Normal Prostatic Epithelial Cells by Liposomes Containing Large T–SV40 Gene", *J. Urol.*, 146(3), 881–886 (Sep. 1991).

Defer et al., "Human Adenovirus–Host Cell Interactions: Comparative Study with Members of Subgroups B and C", *J. Virol.*, 64, 3661–3673 (1990).

Felgner et al., "Lipofection: A Highly Efficient, Lipid–Mediated DNA–Transfection Procedure", *Proc. Natl. Acad. Sci.*, 84, 7413–7417 (1987).

Fernandez–Puentes et al., "Viral Infection Permeabilizes Mammalian Cells to Protein Toxins", *Cell*, 20, 769–775 (1980).

FitzGerald et al., "Adenovirus–Induced Release of Epidermal Growth Factor and Pseudomonas Toxin into the Cytosol of KB Cells During Receptor–Mediated Endocytosis", *Cell*, 32, 607–617 (1983).

Gareis et al., "Homologous Recombination of Exogenous DNA Fragments with Genomic DNA in Somatic Cells of Mice", *Cell. Mol. Biol.*, 37(2), 191–203 (1991).

Glushakova et al., "Optimization of the Transfer and Incorporation of Viral DNA into Cells using Liposomes Conjugated with Influenza Virus Glycoprotein", *Mol. Gen. Mikrobiol. Virusol.*, 7, 32–36 (Jul. 1985) (only abstract available).

Graham et al., "A New Technique for the Assay of Infectivity of Human Adenovirus 5 DNA", *Virology*, 52, 456–467 (1973).

Hartig et al., "Generation of Recombinant Baculovirus via Liposome–Mediated Transfection", *Biotechniques*, 11(3), 310–313 (Sep. 1991).

Hawley–Nelson et al., "LipofectAMINE® Reagent: A New, Higher Efficiency Polycationic Liposome Transfection Reagent", *Focus*, 15, 73–79 (1993).

Helenius et al., "Endosomes", *Trends Biochem. Sci.*, 8, 245–250 (1983).

Inumaru et al., "Characterization of Pseudorabies Virus Neutralization Antigen Glycoprotein gIII Produced in Insect Cells by a Baculovirus Expression Vector", *Virus Res.*, 21(2), 123–39 (1991).

Kato et al., "Expression of Hepatitus B Virus Surface Antigen in Adult Rat Liver", *J. Biolog. Chem.*, 266(6), 3361–3364 (1991).

Kato et al., "Establishment of Hepatitis B Virus Model Animals by HBJ–Liposome Method", *Nippon Rinsho*, 51(2), 525–30 (Feb. 1993) (only abstract available).

Kato et al., "Use of the Hemagglutinating Virus of Japan (JBJ)–liposome Method for Analysis of Infiltrating Lymphocytes Induced by Hepatitis B Virus Gene Expression in Liver Tissue", *Biochim. Biophys. Acta*, 1182(3), 283–90 (Oct. 1993).

Kislina et al., "Effectiveness of Incorporation of Spermine–Condensed Viral DNA into Liposomes, Interaction of Liposomes with Cells", *Gen. Mikrobiol. Virusol.*, 2, 17–21 (Feb. 1985) (only abstract available).

Lee et al., "In Vivo Adenoviral Vector–Mediated Gene Transfer into Balloon–Injured Rat Carotid Arteries", *Circ. Res.*, 73(5), 797–807 (Nov. 1993).

Li et al., "Gene Transfer in Primary Cultures of Human Hepatocytes", *In Vitro Cell Dev. Biol.*, 28A(5), 373–5 (May 1992).

May et al., "Cationic Liposomes Enable Bovine Herpesvirus Type 2 DNA to Infect Cells", Letter to the Editor, *Acta Virol.*, 35, 107 (1991).

Nabel et al., "Direct Transfer of Transforming Growth Factor β1 Gene into Arteries Stimulates Fibrocellular Hyperplasia", *Proc. Natl. Acad. Sci.*, 90, 10759–10763 (1993).

Nabel et al., "Direct Gene Transfer with DNA–Liposome Complexes in Melanoma: Expression, Biologic Activity, and Lack of Toxicity in Humans", *Proc. Natl. Acad. Sci.*, 90, 11307–11311 (1993).

Otero et al., "Proteins are Co–Internalized with Virion Particles During Early Infection", *Virology*, 160, 75–80 (1987).

Pastan et al., "Adenovirus Entry into Cells: Some New Ovservations on an Old Problem", In: *Concepts in Viral Pathogenesis II*, Notkins et al., ed., (NY: Springer–Verlag, 1986) 141–147.

Persson et al., "Virus–Receptor Interaction in the Adenovirus System: Characterization of the Positive Cooperative Binding of Virions on HeLa Cells", *J. Virol.*, 54, 92–97 (1985).

Quantin et al., "Adenovirus as an Expression Vector in Muscle Cells In Vivo", *Proc. Natl. Acad. Sci.*, 89, 2581–2584 (1992).

Rosenfeld et al., "Adenovirus–Mediated Transfer of a Recombinant Antitrypsin Gene to the Lung Epithelium In Vivo", *Science*, 252, 431–434 (1991).

Rosenfeld et al., "In vivo Transfer of the Human Cystic Fibrosis Transmembrane Conductance Regulator Gene to the Airway Epithelium", *Cell*, 68, 143–155 (1992).

Seth et al., "Evidence that the Penton Base of Adenovirus is Involved in Potentiation of Toxicity of Pseudomonas Exotoxin Conjugated to Epidermal Growth Factor", *Mol. Cell. Biol.*, 4, 1528–1533 (1984).

Seth et al., "Role of a Low–pH Environment in Adenovirus Enhancement of the Toxicity of a Pseudomonas Exotoxin–Epidermal Growth Factor Conjugate", *J. Virol.*, 51, 650–655 (1984).

Seth et al., "Adenovirus–Dependent Release of $^{51}$Cr From KB Cells at an Acidic pH", *J. Biol. Chem.*, 259, 14350–14353 (1984).

Seth et al., "Adenovirus–Dependent Increase in Cell Membrane Permeability", *J. Biol. Chem.*, 260, 9598–9602 (1985).

Seth et al., "Binding of Adenovirus and its External Proteins to Triton X–114", *J. Biol. Chem.*, 260, 14431–14434 (1985).

Seth et al., "Pathway of Adenovirus Entry into Cells", In: *Virus Attachment and Entry into Cells*, Colwell et al., eds., (Washington, D.C.: American Society for Microbiology, 1986) 191–195.

Seth et al., "Adenovirus–Dependent Changes in Cell Membrane Permeability; Role of Na$^+$, K$^+$–ATPase", *J. Virol.*, 61, 883–888 (1987).

Seth et al., "Mechanism of Enhancement of DNA Expression Consequent to Cointernalization of a Replication–Deficient Adenovirus and Unmodified Plasmid DNA", *J. Virol.*, 68(2), 933–940, (Feb. 1994).

Seth, "Adenovirus–Dependent Release of Choline from Plasma Membrane Vesicles at an Acidic pH Is Mediated by the Penton Base Protein", *J. Virol.*, 68(2), 1204–1206 (Feb. 1994).

Shimura et al., "Selective Cytotoxicity of Phospholipids and Diacylglycerols to Rat 3Y1 Fibroblasts Transformed by Adenovirus Type 12 or its E1A Gene", *Cancer Research*, 48, 578–583 (1988).

Steinhauer et al., "Deacylation of the Hemagglutinin of influenza A/Aichi/2/68 has no Effect on Membrane Fusion Properties", *Virology*, 184(1), 445–448 (Sep. 1991).

Tikchonenko et al, "Transfer of Condensed Viral DNA into Eukaryotic Cells Using Proteoliposomes", *Gene*, 63, 321–330 (1988).

Tomita et al., "Direct in vitro Gene Introduction into Rat Kidney", *Biochem. Biophys. Res. Comm.*, 186, 129–134 (1992).

Wagner et al., "Coupling of Adenovirus to Transferrin–Polylysine/DN Complexes Greatly Enhances Receptor–Mediated Gene Delivery and Expression of Transfected Genes", *Proc. Natl. Acad. Sci. USA*, 89, 6099–6103 (1992).

Wickman et al., "Integrins $a_v\beta_3$ and $a_v\beta_5$ Promote Adenovirus Internalization but not Virus Attachment", *Cell*, 73, 309–319 (Apr. 23, 1993).

Wolff et al., "Gene Direct Transfer into Mouse Muscle in Vivo", *Science*, 247, 1465 (1990).

Yamaizumi et al., "Macromolecules can Penetrate the Host Cell Membrane During the Early Period of Incubation with HVJ (Sendai Virus)", *Virology*, 95, 218–221 (1979).

Yoshimura, "Adenovirus–Induced Leakage of Co–Endocytosed Macromolecules into the Cytosol", *Cell Struct. Funct.*, 10, 391–404 (1985).

Yoshimura et al., "Adenovirus–Mediated Augmentation of Cell Transfection with Unmodified Plasmid Vectors", *J. Biol. Chem.*, 268, 2300–2303 (1993).

Yu et al., "Genetic Engineering of a Lymantria Dispar Nuclear Polyhedrosis Virus for Expression of Foreign Genes", *J. Gen. Virol.*, 73(6), 1509–14 (Jun. 1992).

Seth et al., *J. Cell Biochem.* (Keystone Symposium on Gene Therapy, Colorado, Apr. 12–18, 1993), *Suppl. 17E*, p. 251 (1993).

Hawley–Nelson et al., FASEB J., 7(3):A167 (1993).

Ciccarone et al., FASEB J., 7(7):A1131 (1993).

Chytil et al., Mol. Biol. Cell, 3:90a (1992).

Hawley–Nelson et al., Mol. Biol. Cell, 4:225 (1993).

Zatloukal et al., Annals New York Academy of Sciences, 660:136–153 (1992).

Cristiano et al., Proc. Natl. Acad. Sci. USA, 90: 2122–2126 (1993).

Zatloukal et al., Gene, 135:199–207 (1993).

Seth, P., Biochemical and Biophysical Research Communications, 205(2):1318–1324 (1994).

METHOD OF ADENOVIRAL-MEDIATED CELL TRANSFECTION

TECHNICAL FIELD OF THE INVENTION

The present invention relates to transfection of eukaryotic cells with nucleic acids mediated by an adenovirus, and the augmentation of such transfection through preincubation of the nucleic acids with cationic agents.

BACKGROUND OF THE INVENTION

Research of the past decade evinces a strong and ongoing interest in devising new and better methods for introducing biological materials, in particular, nucleic acids, such as ribonucleic acid (RNA), deoxyribonucleic acid (DNA), and, more recently, peptide nucleic acid (PNA), into eukaryotic cells. Such methods are prerequisites not only for so-called simple gene transfections in vitro, but also for a true understanding of gene function (which requires, in part, an ability to deliberately modify the genome) directed toward an ultimate goal of augmentation therapy or, more preferably, somatic gene modification or therapy in vivo, to correct the underlying defect in inheritable diseases (IDs). Although, many techniques such as use of DEAE-dextran, electroporation, calcium phosphate, microinjection, and osmotic shock are available for in vitro nucleic transfer, these methods are of limited use for in vivo nucleic acid transfer as they are either toxic to cells or their efficiencies of nucleic acid transfer are low (Felgner et al., *Proc. Natl. Acad. Sci.*, 84, 7413–7417 (1987)).

Consequently, "early" researchers of gene therapy (i.e., those within the last few years) resorted to use of retroviral vectors, which are capable of effecting their own means of entry into cells. In the predominant approach to gene modification, researchers almost exclusively delivered nucleic acids ex vivo to isolated cells, and then infused the cells back into the living host. However, retroviruses have a number of drawbacks which severely limit their application, particularly in vivo. For example, since retroviral vectors require target cell proliferation in order to transfer exogenous nucleic acid sequences, they are ineffective for transferring nucleic acids to cells which replicate slowly or are terminally differentiated (Mastrangeli et al., *J. Clin. Invest.*, 91, 225–34 (1993)). Additionally, they integrate randomly into the genome, potentially resulting in loss of control of the subcloned DNA, as well as host genetic alterations due to the disruption of genes. Moreover, retroviruses exhibit restricted host cell range and can be obtained only in relatively low titer (Burns et al., *Proc. Natl. Acad. Sci.*, 90, 8033–37 (1993)).

Consequently, many researchers turned to adenovirus (Ad) to resolve this dilemma, since host cell proliferation is not required for adenoviral gene expression (Horwitz, In: *Virology*, 2nd Ed., Fields et al., eds., (New York: Raven Press, 1990) 1679–1721; Berkner, K. L., *BioTechniques*, 6, 606–629 (1988)). Furthermore, Ad possesses tremendous potential for eukaryotic studies given that it can infect a broad range of cell types from a variety of diverse species, it is easy to prepare in high titer, and it can easily be rendered replication-deficient, thus preventing the virus from usurping, and eventually destroying, the target cell (Ginsberg (ed.) *The Adenoviruses*, (New York: Plenum Press, 1984); Horwitz, In: *Virology*, 2nd Ed., Fields et al., eds., (New York: Raven Press, 1990) 1679–1721; Rosenfeld et al., *Science*, 252, 431–434 (1991); Rosenfeld et al., *Cell*, 68, 143–155 (1992); Quantin et al., *Proc. Natl. Acad. Sci.*, 89, 2581–2584 (1992)).

Additional advantages of adenoviral vectors include that recombination events are rarely observed with use of such vectors. Moreover, despite ubiquitous infection with adenoviruses, an association of such infections with any human malignancy has not been demonstrated. In fact, the live (or non-attenuated) form of adenovirus has been safely employed as a human vaccine ((Horwitz, In: *Virology*, 2nd Ed., Fields et al., eds., (New York: Raven Press, 1990) 1679–1721; Berkner, K. L., *BioTechniques*, 6, 606–629 (1988); Ginsberg (ed.) *The Adenoviruses*, (New York: Plenum Press, 1984)). Furthermore, adenovirus exhibits trophism for the respiratory epithelium, and can be transcribed, translated, and appropriately processed in lung, gastrointestinal (GI), as well as a variety of other types of tissue (Fields et al., eds., (New York: Raven Press, 1990) 1679–1721; Crystal et al., *Nucleic Acids Res.*, 21, 1607–12 (1993)). All these factors suggest that adenovirus constitutes a powerful tool in somatic gene therapy of IDs, particularly those which manifest in disorders of the lung and GI tract.

Human adenovirus exists as a non-enveloped double-stranded DNA virus (Horwitz, In: *Virology*, 2nd Ed., Fields et al., eds., (N.Y.: Raven Press, 1990) 1679–1721). The adenovirus provides a dramatic example of a naturally evolved and highly efficient mechanism for transferring biological materials to target cells (Otero et al., *Virology*, 160, 75–80 (1987); FitzGerald et al., *Cell*, 32, 607–617 (1983); Seth et al., *Mol. Cell Biol.*, 4, 1528–1533 (1984); Yoshimura, *Cell Struct. Funct.*, 10, 391–404 (1985); Defer et al., *J. Virol.*, 64, 3661–3673 (1990); Rosenfeld et al., *Science*, 252, 431–434 (1991); Curiel et al., *Proc. Natl. Acad. Sci.*, 88, 8850–8854 (1991); Rosenfeld et al., *Cell*, 68, 143–155 (1992); Quantin et al., *Proc. Natl. Acad. Sci.*, 89, 2581–2584 (1992); Curiel et al., *Hum. Gene Therapy*, 3, 147–154 (1992)). Namely, Ad enters cells by a receptor-mediated endocytosis (RME) pathway. In the initial virus-receptor interaction in this pathway, Ad binds with specific receptors present on the cell surface via fibers on its outer surface (i.e., the outer shell of each Ad is comprised of 240 hexons and 12 pentons, with each penton being composed of a penton base and a fiber) (Ginsberg (ed.) *The Adenoviruses*, (New York: Plenum Press, 1984); Horwitz, In: *Virology*, 2nd Ed., Fields et al., eds., (New York: Raven Press, 1990) 1679–1721; Seth et al., In: *Virus Attachment and Entry into Cells*, Colwell et al., eds., (WA, D.C.: American Society for Microbiology, 1986) 191–195. Following attachment, the receptors with bound Ad cluster in coated pits, and the virus is internalized within a clathrin-coated vesicle and, subsequently, into an endosomal vesicle, termed an endosome, or receptosome (FitzGerald et al., *Cell*, 32, 607–617 (1983)).

Within the endosome, the pH of the vesicle is reduced by means of a proton pump associated with the endosomal membrane. The reduced pH effects an alteration in the conformation of the Ad capsid proteins, particularly the penton base protein, which results in disruption of the endosome. As a consequence of this disruption, the endocytic contents, including the Ad, are released into the cytoplasm, and the Ad is then translocated to the nucleus where it directs the synthesis of nascent nucleic acids (FitzGerald et al., *Cell*, 32, 607–617 (1983); Seth et al., *Mol. Cell Biol.*, 4, 1528–1533 (1984); Seth et al., In: *Virus Attachment and Entry into Cells*, Colwell et al., eds., (WA, D.C.: American Society for Microbiology, 1986) 191–195; Seth et al., *J. Virol.*, 51, 650–655 (1984); Seth et al., *J. Biol. Chem.*, 259, 14350–14353 (1984); Seth et al., *J. Biol. Chem.*, 260, 9598–9602 (1985); Seth et al., *J. Biol. Chem.*, 260, 14431–14434 (1985); Blumenthal et al., *Biochemistry*, 25, 2231–2237 (1986); Seth et al., *J. Virol.*, 61, 883–888 (1987)).

This ability of the Ad to easily enter cells has been seized upon as a means of transporting macromolecules into cells (Otero et al., *Virology*, 160, 75–80 (1987); FitzGerald et al., *Cell*, 32, 607–617 (1983); Seth et al., *Mol. Cell Biol.*, 4, 1528–1533 (1984); Yoshimura, *Cell Struct. Funct.*, 10, 391–404 (1985); Defer et al., *J. Virol.*, 64, 3661–3673 (1990); Rosenfeld et al., *Science*, 252, 431–434 (1991); Curiel et al., *Proc. Natl. Acad. Sci.*, 88, 8850–8854 (1991); Rosenfeld et al., *Cell*, 68, 143–155 (1992); Quantin et al., *Proc. Natl. Acad. Sci.*, 89, 2581–2584 (1992); Curiel et al., *Hum. Gene Therapy*, 3, 147–154 (1992)). For example, Ads are able to enhance the transfer of a variety of non-viral macromolecules such as dextrans (Otero et al., *Virology*, 160, 75–80 (1987)), proteins (Carrasco, *Virology*, 113, 623–629 (1981); Defer et al., *J. Virol.*, 64, 3661–3673 (1990); FitzGerald et al., *Cell*, 32, 607–617 (1983); Fernandez-Puentes et al., *Cell*, 20, 769–775 (1980); Otero et al., *Virology*, 160, 75–80 (1987)), and plasmid DNA linked to ligands (Curiel et al., *Hum. Gene Therapy*, 3, 147–154 (1992); Cotten et al., *Proc. Natl. Acad. Sci.*, 89, 6094–098 (1992)) to target cells both in vitro and in vivo.

There are two means by which such transfer has been effected. First, the Ad has been employed to transfer non-viral macromolecules packaged within the Ad either in place of, or in addition to, normal Ad components (Berkner, K. L., *BioTechniques*, 6, 606–629 (1988)). For example, the genome of the Ad has been modified to incorporate exogenous DNA. The recombinant Ad is then packaged to constitute an infectious virus capable of entering cells and transferring the exogenous DNA to the nucleus (Rosenfeld et al., *Science*, 252, 431–434 (1991); Rosenfeld et al., *Cell*, 68, 143–155 (1992); Quantin et al., *Proc. Natl. Acad. Sci.*, 89, 2581–2584 (1992); Berkner, K. L., *BioTechniques*, 6, 606–629 (1988)). Second, the Ad has been employed to mediate the transfer of non-viral macromolecules either linked to the surface of the Ad or, in a "bystander" process where the macromolecule is cointernalized, taken along as cargo in the Ad receptor-endosome complex (Otero et al., *Virology*, 160, 75–80 (1987); FitzGerald et al., *Cell*, 32, 607–617 (1983); Seth et al., *Mol. Cell Biol.*, 4, 1528–1533 (1984); Yoshimura, *Cell Struct. Funct.*, 10, 391–404 (1985); Defer et al., *J. Virol.*, 64, 3661–3673 (1990)).

The mechanism by with the Ad augments internalization of non-viral biologic materials is believed to be by increasing the permeability of the target cell plasma membrane (Otero et al., *Virology*, 160, 75–80 (1987)) or, more likely, by cointernalization of the exogenous biologic material as an "innocent bystander" when the Ad-receptor complexes cluster on the membrane and are internalized (FitzGerald et al., *Cell*, 32, 607–617 (1983); Seth et al., *Mol. Cell Biol.*, 4, 1528–1533 (1984); Yoshimura, *Cell Struct. Funct.*, 10, 391–404 (1985); Otero et al., *Virology*, 160, 75–80 (1987); Defer et al., *J. Virol.*, 64, 3661–3673 (1990)). These processes are not Ad-specific, as similar phenomena have been observed with other non-enveloped viruses such as picornavirus (Fernández-Puentes et al., *Cell*, 20, 769–775 (1980); Otero et al., *Virology*, 160, 75–80 (1987); Carrasco, *Virology*, 113, 623–629 (1981)), as well as enveloped viruses including paramyxovirus, rhabdovirus, poxvirus, and togavirus (Fernández-Puentes et al., *Cell*, 20, 769–775 (1980); Otero et al., *Virology*, 160, 75–80 (1987); Yamaizumi et al., *Virology*, 95, 216–221 (1979); Carrasco et al., *Virology*, 117, 62–69 (1982)).

Most of the research attention on virus-mediated cointernalization of macromolecules has been focused on cointernalization of proteins, including toxins and various reporter proteins (Ferná-Puentes et al., *Cell*, 20, 769–775 (1980); FitzGerald et al., *Cell*, 32, 607–617 (1983); Seth et al., *Mol. Cell Biol.*, 4, 1528–1533 (1984); Otero et al., *Virology*, 160, 75–80 (1987); Defer et al., *J. Virol.*, 64, 3661–3673 (1990); Carrasco, *Virology*, 113, 623–629 (1981); Yamaizumi et al., *Virology*, 95, 216–221 (1979); Carrasco et al., *Virology*, 117, 62–69 (1982)). The concept that cointernalization might be employed for Ad-mediated transfer of nucleic acids was suggested, but not evaluated, by Otero and Carrasco (Otero et al., *Virology*, 160, 75–80 (1987)). In fact, the more recent approaches with respect to transfer of nucleic acids using adenovirus have centered on nucleic acid transfer by attachment of the nucleic acid to molecules capable of effecting its entry into the cell. For instance, in one approach, the nucleic acid is part of a polylysine-glycoprotein carrier complex capable of binding a particular cell surface receptor, or is complexed with a nonspecific ligand such as a charged polypeptide (Rosenfeld et al., *Science*, 252, 431–434 (1991); Curiel et al., *Proc. Natl. Acad. Sci.*, 88, 8850–8854 (1991); Rosenfeld et al., Cell, 68, 143–155 (1992); Quantin et al., *Proc. Natl. Acad. Sci.*, 89, 2581–2584 (1992); Curiel et al., *Hum. Gene Therapy*, 3, 147–154 (1992)); Cotten et al., *Proc. Natl. Acad. Sci.*, 89, 6094–098 (1992); Cotten et al., *J. Virology*, 67, 3777–3785 (1993)). In a more recent approach, the nucleic acid is attached to the outside of the adenoviral capsid by means of conjugation of the nucleic acid through a polylysine residue to the antibody to adenoviral capsid protein (Curiel et al., *Human Gene Ther.*, 3, 147–154 (1992)). Thus, despite this early suggestion by Otero et al., researchers have clearly perceived a lack of feasibility of using adenovirus-driven RME for transfer of nucleic acid. Moreover, the prevailing approaches using adenovirus for transfer of nucleic acids are limited in that the specific receptor to the ligand employed (e.g., transferring must be present on the cell surface for transfection to be accomplished. Additionally, it was discovered recently that better transfection results are obtained when the DNA is not physically attached to any molecule upon introduction into the cell (Wolff et al., *Science*, 247, 1465 (1990); Acsadi et al., *Nature*, 352, 815 (1991)). This finding underscores the restrictive nature of current approaches to adenoviral-mediated transfer of DNA to the cell, which require attachment of DNA for cell transfection.

In an essential mimic of the approach of using an adenovirus as a vector, the nucleic acid to be transfected is ensheathed in a virion-like microenvironment. The encased nucleic acid may then be transferred via intracellular injection or, optimally, spontaneous fusion with the cellular membrane. (Nabel et al., *Proc. Natl. Acad. Sci.*, 90, 10759–10763 (1993); Nabel et al., *Proc. Natl. Acad. Sci.*, 90, 11307–11311 (1993)). The microenvironment may be comprised of liposomes or hollow vesicles synthesized using lipids and/or phospholipids (Tikchonenko et al., *Gene*, 63, 321–330 (1988); Hawley-Nelson et al., *Focus*, 15, 73–79 (1993); Felgner et al., *Proc. Natl. Acad. Sci.*, 84, 7413–7417 (1987); U.S. Pat. No. 5,264,618). While such an approach is advantageous in that potentially greater amounts of nucleic acids can be transferred, disadvantages of the approach include failure of the liposome to fuse with the cell membrane and degradation of nucleic acids taken up by phagocytosis, and the inherent toxicity of intracellular injection, as well as the toxicity of ether bonds, which may accumulate in the cell as a consequence of liposome-mediated transfection.

Attempts have been made to enhance the ability of the liposomes to fuse with the membrane through subsequent infection with, for example, Sendai virus (Tomita et al., *Biochem. Biophys. Res. Comm.*, 186, 129–34 (1992); Kato et al., *J. Biolog. Chem.*, 266, 3361–364 (1991); Yamaizumi et al., *Virology*, 95, 218–221 (1979)). However, studies supporting the increased cytotoxicity of exogenously supplied liposomes to cells transformed with adenovirus (Shimura et al., *Cancer Research*, 48, 578–583 (1988)), suggest against the combination of adenoviral-mediated nucleic acid transfer with liposome-mediated nucleic acid delivery.

There remains a need, therefore, for a method of capitalizing on the inherent ability of adenovirus to effect transport of cargo macromolecules to the cell nucleus by means of RME in a method of transfection that can be employed either in vitro or in vivo, and which avoids the attendant problems of the previously described approaches. It is an object of the present invention to provide such a method of adenoviral-mediated cell transfection with nucleic acids, as well as to provide a means of enhancing this method through use of cationic agents. These and other objects and advantages of the present invention, as well as additional inventive features, will be apparent from the description of the invention provided herein.

BRIEF SUMMARY OF THE INVENTION

The present invention provides an adenoviral-mediated method of transfection with nucleic acids which can be augmented through incubation of the nucleic acids with cationic agents. Specifically, the present inventive method of introducing a nucleic acid into a eukaryotic cell comprises contacting the cell with, in any order or simultaneously, the nucleic acid and an adenovirus, wherein the nucleic acid is not bound to any molecule capable of effecting its entry into the cell. The cell is preferably additionally contacted with a cationic agent, such as a monocationic or polycationic liposome, such that the nucleic acid is not bound to any molecule capable of effecting its entry into the cell other than, optionally, the cationic agent.

Figure 1:
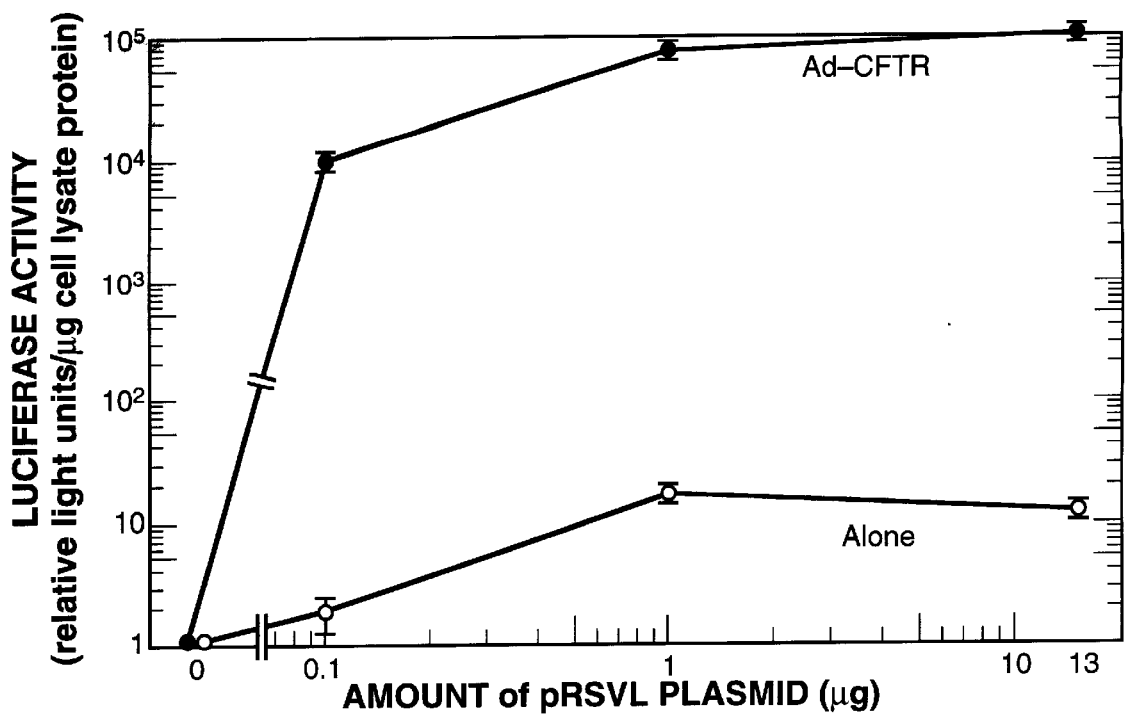
FIG. 1 is a graph of pRSVL amount ($\mu$g) versus luciferase activity (RLU/$\mu$g cell lysate protein) for COS-7 cells incubated with increasing amounts of pRSVL plasmid alone ($\circ$) or prior to infection with Ad-CFTR ($\bullet$).

for IB3-1 cells incubated with pCMVCFTR alone (A), plus either Ad.RSVβgal (B), or liposomes comprised of a 1:1 molar DOSPA:DOPE ratio (C), or with the liposomes as well as the pCMVCFTR and Ad.RSVβgal plasmids (D) for 24 hours, followed by another 18 hours incubation with SPQ (portion of the graph labeled 'iodide'), followed by incubation in buffer in which NaCl was replaced with NaNO$_3$ (portion of the graph labeled 'nitrate'), followed by incubation in buffer solution containing 20 μM forskolin, 200 μM cpt-cAMP, and 500 μM IBMX (portion of the graph labeled 'cpt-cAMP+IBMX+FSK').

DETAILED DESCRIPTION OF THE INVENTION

The present invention relates to a method of transferring nucleic acids to eukaryotic cells, which is mediated by adenovirus, and which may be further augmented through incorporation of cationic agents in the transfection reaction. Transfection refers to the transfer of nucleic acids into a cell by any means. In the context of the present invention, a cationic agent is a substance which carries a positive charge that enables it to interact with anionic nucleic acids as well as, optimally, to spontaneously attach to negatively-charged cell surfaces. Cationic agents include monocationic liposomes, polycationic liposomes, polycarbenes, carbohydrates, polyamino acids, and other positively-charged species that may be capable of interacting with anionic nucleic acids, such as spermine and calcium phosphate. Accordingly, the present invention provides, among other things, a method of adenoviral-mediated transfection of nucleic acids, as well as augmentation of such transfection with cationic agents.

For ease of reference, the abbreviations used herein are as indicated in Table 1.

TABLE 1

| Abbreviations | |
|---|---|
| ATCC | American Type Culture Collection |
| cDNA | complementary deoxyribonucleic acid |
| CF | cystic fibrosis |
| CFTR | cystic fibrosis transmembrane conductance regulator |
| CS | calf serum |
| DDAB | dioctadecylammonium bromide |
| DMEM | Dulbecco's modified Eagle medium |
| DNA | deoxyribonucleic acid |
| DOGS | dioctadecylamidoglycylspermine |
| DOPE | dioleoylphosphatidyl ethanolamine |
| DORI ETHER | 1,2-dioleyl-3-dimethylamino propyl-B-hydroxy-ethylammonium acetate |
| DORI ETHER Bromo | |
| DORI ETHER Propylamine | N-[2-[(3-aminopropyl)amino]ethyl]-N,N-dimethyl-2,3-bis(octdecenyloty)-1-propaninium dibromide |
| DOSPA | 2,3-dioleyloxy-N -[2-(sperminecarboxamido)ethyl]-N,N-dimethyl 1-propanaminium trifluoroacetate |
| DOTAP | (1,2-bis(oleoyloxy)-3(trimethylammonio)propane |
| DOTMA | N-[1-(2,3-diolyeyloxy)propyl]-N,N,N-trimethylammonium chloride |
| FBS | fetal bovine serum |
| FCS | fetal calf serum |
| GI | gastrointestinal |
| HEPES | N'-2-hydroxyethylpiperazine-N'-2-ethanesulfonic acid |
| kb | kilobase pairs |
| kDa | kilodalton |
| IBMX | 3-isobutyl-1-methylxanthine |

TABLE 1-continued

| Abbreviations | |
|---|---|
| ID | inheritable disease |
| IMEM | improved modified Eagle medium |
| ONPG | o-nitrophenyl β-D-galactopyranoside |
| PBS | phosphate buffered saline |
| PFU | plaque-forming units |
| PNA | peptide nucleic acid |
| RLU | relative light units |
| RME | receptor-mediated endocytosis |
| RNA | ribonucleic acid |
| SDS | sodium dodecyl sulfate |
| SPQ | (6-methoxy-N-(3-sulfopropyl) quinolinium |
| SV40 | simian virus 40 |
| Tris | tris (hydroxymethyl)aminomethane |
| X-gal | 5-bromo-4-chloro-3-indolyl-β-D-galactopyranoside |

An Ad, unless specified otherwise, is of a human strain and comprises a complete adenoviral virus particle (i.e., a virion) consisting of a core of nucleic acid and a protein capsid. Preferred adenoviral vectors according to this invention include Ad5, Ad-CFTR and Ad-dl312.

For the purpose of this invention, the adenovirus employed for nucleic acid transfer may be wild-type (i.e., replication competent). However, it is not necessary that the genome of the employed adenovirus be intact. In fact, to prevent the virus from usurping host cell functions and ultimately destroying the cell, the adenovirus may be inactivated prior to its use, for example, by UV irradiation. Alternatively, the adenovirus may comprise genetic material with at least one modification therein, which may render the virus replication-deficient.

The modification to the adenoviral genome may include, but is not limited to, addition of a DNA segment, rearrangement of a DNA segment, deletion of a DNA segment, replacement of a DNA segment, methylation of unmethylated DNA, demethylation of methylated DNA, and introduction of a DNA lesion. For the purpose of this invention, a DNA segment may be as small as one nucleotide and as large as 36 kilobase pairs (kb) (i.e., the size of the adenoviral genome) or, alternatively, may equal the maximum amount which can be packaged into an adenoviral virion (i.e., about 38 kb).

Such modifications to the adenoviral genome may render the adenovirus replication-deficient. Alternatively, the modification may alter the ability of the adenovirus to bind to its cell surface receptor, the ability of Ad internalized by RME to escape from the endosome by lysis of same, and the ability of RME to essentially reroute cointernalized nucleic acids from their fated path of intracellular processing (i.e., primarily phagocytic degradation) by allowing the transport of such cargo molecules to the nucleus.

Moreover, in a preferred embodiment of the present invention, the Ad genome is not even present, and the adenovirus employed for nucleic acid transfer is not a complete virion, but comprises instead empty protein capsids. Alternatively, it may be possible to construct artificial capsids, by linking the amino- or carboxyterminal sequences of proteins, peptides or glycoproteins to lipids. The resultant lipid moiety could then be incorporated into a liposome. Such techniques are known in the art, and in fact have been used to construct liposomes carrying influenza virus glycoproteins on their surface (Tikchonenko et al., Gene, 63, 321–330 (1988)).

In another preferred embodiment, the present invention contemplates that the properties of the employed adenovirus (e.g., the cell binding, endosomal lysis or intracellular targeting capabilities of the adenovirus) may be altered not by modification of the adenoviral genome per se, but by use of agents which, although they might in fact alter the genome, primarily act by altering certain properties of the adenovirus. In preferred embodiments of the present invention, adenoviral properties may be altered by heat-treatment, or by exposure to either antiserum to the adenovirus, or chloroquine. Alternatively, the adenovirus may be inactivated by either short-wavelength or long-wavelength UV irradiation (i.e., radiation of viral samples with either UVA, UVB or UVC), which may further be employed in conjunction with other agents which may synergize with UV irradiation in effecting viral inactivation, such as for instance, DNA intercalators, including psoralens (e.g., 8-methoxypsoralen).

The nucleic acid being transferred may comprise DNA, RNA, or PNA which may be as small as one repeat unit (i.e., a nucleotide for DNA and RNA, and a 2-aminoethylglycine unit to which a base is attached for PNA) and as large as can reasonably be isolated or synthesized, or transferred to a host cell using the method of the present invention.

The nucleic acid may constitute or encode sense or antisense sequences, including ribozymes, or catalytic RNA species such as described in the art (Hampel et al., *Nucleic Acids Research*, 18, 299–304 (1990); Cech et al., *Annual Rev. Biochem.*, 55, 599–629 (1986)), as well as engineered sequences, or sequences which are not normally present in vivo. The nucleic acid may be linear, circular, or of any topology. RNA sequences may be unmodified, or may be modified to retard degradation. The invention further contemplates nucleic acids comprised of oligonucleotides (Ts'O et al., *Annals NY Acad. Sci.*, 570, 220–241 (1987)).

Nucleic acids can be either single-stranded, double-stranded, or triple-stranded, or a mixture of single-, double-, or triple-stranded regions, and may be comprised of more than one type (i.e., DNA, RNA, or PNA) of nucleic acid. Nucleic acids may contain lesions including but not limited to: a missing base or altered base (e.g., an alkylated base), a cyclobutyl dimer, strand breaks, and cross-linking of nucleic acid strands.

The nucleic acid may be present in any type of vector appropriate for introduction of nucleic acids into eukaryotic cells, or may not be subcloned in any vector at all. For example, the following list of vectors which may be employed is by no means exhaustive: mammalian expression vectors, vectors in which the subcloned nucleic acid is under the control of its own cis-acting regulatory elements, and vectors which are designed to facilitate gene integration or gene replacement in host cells.

In the method of the present invention, the nucleic acid may be transferred to a eukaryotic host cell. This eukaryotic host cell may be present in vitro or in vivo. In a preferred embodiment of the present invention, in vivo transfection of nucleic acids is contemplated. However, the method of the present invention also contemplates nucleic acid transfer in vitro.

The method of the present invention can be effectively carried out using a wide variety of different cell types, albeit with differing levels of efficiency. The method can be employed in various cells differing both in number of adenovirus receptors as well as in the affinity of the cell surface receptors for adenovirus. Accordingly, the types of cells to which gene delivery is contemplated in vitro or in vivo in the context of the present invention include avian cells, and mammalian cells including but not limited to rodent, ape, chimpanzee, feline, canine, ungulate (such as ruminant or swine), as well as human cells. Moreover, if nucleic acid transfer to a particular cell type is limited due, for instance, to a lack of receptors for adenovirus, transfer may be increased using methods employed, for example, to carry human adenovirus into blood cells. Namely, the virus can be coupled to a DNA-polylysine complex containing a ligand (e.g., transferrin) for mammalian cells (Wagner et al., *Proc. Natl. Acad. Sci.*, 89, 6099–6103 (1992)).

Adenoviral-mediated transfections and augmentation thereof with cationic agents can be carried out over a range of cell densities. However, the method is particularly appropriate for in vitro transfections when cells are at used a density of about $10^5$ to $10^6$ cells/ml. Eukaryotic cells need not be exponentially growing at the time of transfection, and may even be terminally differentiated.

In a preferred embodiment of the present invention, the method of nucleic acid transfer is accomplished by contacting the eukaryotic cell with the nucleic acid and an adenovirus. In this method, the nucleic acid being transferred is not bound to any molecule capable of effecting its entry into the cell. Thus, this method differs over those previously described, wherein, for example, the nucleic acid is transferred to cells as a consequence of being attached to the outside of an adenoviral capsid (Curiel et al., *Human Gene Ther.*, 3, 147–154 (1992)), or as a result of being part of a polylysine-glycoprotein carrier complex (Cotten et al., *Proc. Natl. Acad. Sci.*, 89, 6094–098 (1992); Curiel et al., *Proc. Natl. Acad. Sci.*, 88, 8850–8854 (1991); Cotten et al., *J. Virology*, 67, 3777–3785 (1993)). However, the method does not preclude modifications to the nucleic acid which do not in and of themselves provide a means of transport for the nucleic acid into the cell, such as, for example, modifications to RNA or oligonucleotides which act to stabilize the resultant modified nucleic acid.

In another preferred embodiment of the present invention, the method of nucleic acid transfer is accomplished by contacting the eukaryotic cell with the nucleic acid, an adenovirus, and a cationic agent. While any suitable cationic agent may be utilized such as a carbohydrate, a polyamino acid, and other cationic agents capable of interacting with anionic nucleic acids, the cationic agent is preferably comprised of a polycarbene, or a liposome, which is essentially a hollow vesicle comprised of one or more layers.

In this preferred method of nucleic acid transfer, the nucleic acid being transferred is not bound to any molecule capable of effecting its entry into the cell, other than, optionally, the cationic agent. It is possible that spontaneous complexes of the cationic agent and the nucleic acid may form since the nucleic acid may be preincubated with the cationic agent; however, such complexes have not been described in the literature as being employed in conjunction with adenovirus as a means of transfecting nucleic acids. This is likely due to evidence of previous studies supporting the increased cytotoxicity of exogenously supplied liposomes to cells transformed with adenovirus (Shimura et al., *Cancer Research*, 48, 578–583 (1988)), and thus suggesting the futility of the present preferred approach to cell transfection using adenoviral infection in combination with nucleic acids preincubated with cationic agents. Thus, this method of nucleic acid transfer, like the other preferred method of nucleic acid transfer not involving cationic agents, differs over previously described methods.

Furthermore, it is even more preferable that the cationic agent employed in the method of the present invention is not bound to any molecule which in and of itself is capable of effecting the entry of substances into the cell. This would preclude use of cationic agents, such as those described in the literature, in which the cationic agent is complexed, for example, with a ligand for a cell surface receptor (e.g., Cotten et al., *Methods in Enzymol.*, 217, 618–645 (1993)). However, these agents do not appear to have been employed in conjunction with adenoviral-mediated cell transfection.

For these embodiments, the contacting of cells with the various components of the present invention may occur in any order, or may occur simultaneously. In a preferred embodiment, the nucleic acid and cationic agent may be mixed together and preincubated prior to contacting the cell. Preferably, the cell may be contacted with the adenovirus less than about 8 hours after, or less than about 8 hours before, the cell is contacted with the nucleic acid, or with the nucleic acid which has been preincubated with a cationic agent. Even more preferably, the cell may be contacted with the adenovirus more than about 2 hours after, or less than about 2 hours before the cell is contacted with the nucleic acid, or with the nucleic acid which has been preincubated with a cationic agent. In a further preferred embodiment of the invention, adenovirus may be employed in an amount of about 10 to about 2000 placque forming units per cell to be contacted.

Cells being contacted in the transfection method of the present invention are cultured in a reduced-serum medium for about 2 hours prior to transfection. Then plasmid (either in the presence or absence of cationic agents) or adenovirus is added to the cells. Following the appropriate length of time, either adenovirus or plasmid accompanied or not by cationic agents, i.e., whichever was not added previously, is applied to the incubation mixture, and the transfection is allowed to proceed for about 8 to 50 hours. During that time, the cell culture medium may optimally be replaced with either DMEM or IMEM supplemented with either FCS or FBS.

The contemplated uses of the present invention comprise use of technology traditionally employed for synthesis and use of cationic agents, as well as emerging technology. Accordingly, the nucleic acids may be preincubated with the cationic agents including liposomes under the appropriate conditions for appropriate lengths of time such as is known in the art and has been described in the literature (e.g., Tikchonenko et al., *Gene,* 63, 321–330 (1988)).

The cationic agent may be comprised of a polycarbene such as 1,5-dimethyl-1,5-diazaundecamethylene polymethobromide, or polybrene. Alternatively, the cationic agent may be a liposome. The liposome may be comprised of one or a mixture of agents which are appropriate for liposome formation and are known in the art, such as lipids, phospholipids, cholesterol, etc.

Preferably, the liposome of the present invention is comprised of lipid. The lipid may be positively charged, negatively charged, or neutral. Neutral and negatively charged lipids include but are not limited to phospholipids or mono-, di-, or triacylglycerols. The positively charged lipid may be such as is included in a monocationic and polycationic liposome.

The cationic agent may be a monocationic liposome. Preferred monocationic liposomes include liposomes comprised of the lipids N-[1-(2,3-dioleyloxy)propyl]-N,N,N-trimethylammonium chloride (i.e., DOTMA, or Lipofectin® Reagent), 1,2-bis(oleoyloxy)-3-(trimethylammonio)propane (i.e., DOTAP), and a 2:1 molar ratio of 1,2-dioleyl-3-dimethylamino propyl-B-hydroxy-ethylammonium acetate (i.e., DORI ETHER) and dioleoylphosphatidyl ethanolamine (i.e., DOPE), which together comprise the agent 143–7. Liposomes suitable for use in the present invention are described in U.S. patent application Ser. No. 07/937,508, as well as U.S. Pat. No. 5,264,618.

The cationic agent may be a polycationic liposome. Preferred polycationic liposomes include liposomes comprised of dioctadecylamidoglycylspermine (DOGS; Transfectam® Reagent), a 1.5:1 molar ratio of the lipids 2,3-dioleyloxy-N-[2(sperminecarboxamido)ethyl]-N,N-dimethyl-1-propanaminium trifluoroacetate (DOSPA) and DOPE (i.e., LipofectAMINE™), or a 1:1 DOSPA:DOPE molar ratio.

The liposomes of the present invention may be used alone, or in combination with liposomes comprised of other cationic lipids. Liposomes comprised of lipids having metabolizable ester bonds are preferred for in vivo use.

The cationic agent of the present invention may also be comprised of a carbohydrate, including but not limited to DEAE-dextran, and a polyamino acid, including but not limited to poly-L-ornithine. Additionally, the cationic agent may be comprised of other positively-charged species that may be capable of interacting with anionic nucleic acids, such as spermine and calcium phosphate. These cationic agents may be used alone, or in combination with other agents, particularly other cationic agents. The cationic agents may be used as is known and described in the prior art (e.g., Tikchonenko et al., *Gene,* 63, 321–330 (1988); U.S. Pat. No. 5,264,618; Sambrook et al. (eds.), *Molecular Cloning: A Laboratory Manual,* (New York: Cold Spring Harbor Laboratory Press, 1989).

The compositions of the present invention (i.e., compositions comprising a nucleic acid, an adenovirus, and, preferably, a cationic agent) may be made into pharmaceutical compositions with appropriate pharmaceutically acceptable carriers or diluents, and where appropriate, may be formulated into preparations in solid, semi-solid, liquid or gaseous forms such as tablets, capsules, powders, granules, ointments, solutions, suppositories, injections, inhalants, and aerosols, in the usual ways for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions may be used alone or in appropriate association, as well as in combination with, other pharmaceutically active compounds. For example, in applying the method of the present invention for delivery of a nucleic acid encoding CFTR to cells lacking same, such delivery may be employed in conjunction with other means of treatment of CFTR deficiency, such as, for example, treatment with dornase alfa (or Pulmozyme), a recombinant human DNase that liquefies the thick mucous in the lungs of CF patients.

Accordingly, the pharmaceutical compositions of the present invention can be delivered via various routes and to various sites in an animal body to achieve a particular effect. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular effect to be achieved and the particular pharmacodynamics associated with the pharmaceutical composition in the particular host.

Accordingly, the present invention also provides a method of transferring nucleic acids to a host, which comprises administering the composition of the present invention using any of the aforementioned routes of administration or alternative routes known to those skilled in the art and appropriate for a particular application. The "effective amount" of the composition is such as to produce the desired effect in a host which can be monitored using several end-points known to those skilled in the art. For example, one desired effect might comprise effective nucleic acid transfer to a host cell. Such transfer could be monitored in terms of a therapeutic effect (e.g. alleviation of some symptom associated with the ID being treated), or by further evidence of the transferred gene or expression of the gene within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). Three such particularized assays described in the Examples which follow include the assay for expression of the β-galactosidase or luciferase reporter genes, and the assay for cAMP-stimulated $Cl^-$ efflux in certain cells.

These methods described are by no means all-inclusive, and further methods to suit the specific application will be apparent to the ordinary skilled artisan. Moreover, the effective amount of the compositions can be further approximated through analogy to compounds known to exert the desired effect (e.g., Pulmozyme treatment of a fibrotic patient might provide some guidance in terms of the amount of a CFTR nucleic acid to be administered to a host).

Furthermore, the amounts of each active agent included in the compositions employed in the examples described herein (i.e., per each cell to be contacted, about 10 to 2000 adenoviral PFU, and more preferably, about 10 to 1000 adenoviral PFU; and about 0.1 to 20 μg per million cells to be contacted) provide general guidance of the range of each component to be utilized by the practitioner upon optimizing the method of the present invention for practice either in vitro or in vivo. Moreover, such ranges by no means preclude use of a higher or lower amount of a component, as might be warranted in a particular application. For example, the actual dose and schedule may vary depending on whether the compositions are administered in combination with other pharmaceutical compositions, or depending on interindividual differences in pharmacokinetics, drug disposition, and metabolism. Similarly, amounts may vary in in vitro applications depending on the particular cell line utilized (e.g., based on the number of adenoviral receptors present on the cell surface, or the ability of the particular plasmid employed for nucleic acid transfer to replicate in that cell line) or the type of cationic agent employed.

Furthermore, the amount of nucleic acid to be added per cell will likely vary with the length and stability of the nucleic acid, as well as also the nature of the sequence, and is particularly a parameter which needs to be determined empirically, and may be altered due to factors not inherent to the method of the present invention (e.g., the cost associated with synthesis, for instance). One skilled in the art can easily make any necessary adjustments in accordance with the necessities of the particular situation.

The following examples further illustrate the present invention but, of course, should not be construed as in any way limiting its scope.

EXAMPLE 1

Adenoviral Mediated Augmentation of Cell Transfection with pRSVL

This Example confirms that exposure of target cells to an Ad and an unlinked and unmodified plasmid vector results in the enhancement of the expression of a reporter gene contained within the plasmid as compared with exposure of the cells to the plasmid alone.

The cell cultures described herein were employed in most of the Examples which follow. The Ad Type 5 (i.e., Ad5)-transformed human embryonic kidney cell line 293 (American Type Culture Collection (ATCC), CRL 1573) (Graham et al., *J. Gen. Virol.*, 36, 59–72 (1977)) and the human cervical carcinoma cell line HeLa (ATCC CL2) were grown in improved modified Eagle medium (IMEM) containing 10% fetal bovine serum (FBS), 2 mM glutamine, 50 units/ml penicillin, and 50 μg/ml streptomycin (all from Biofluids, Rockville, Md.). COS-7 (ATCC CRL 1561), is a derivative of the African green monkey kidney cell line CV-1 (ATCC CRL70) transformed with a mutant of simian virus 40 (SV40). COS-7 and CV-1 cells were maintained in either Dulbecco's modified Eagle medium (DMEM; BioWhittaker, Inc., Walkersville, Md.) supplemented with 10% FBS, 2 mM glutamate, 100 units/ml penicillin, and 100 μg/ml streptomycin, or in IMEM supplemented with 10% calf serum (CS), 50 units/ml penicillin, and 50 μg/ml streptomycin (all from Biofluids). Cultures were incubated at 37° C. in 10% $CO_2$, unless maintained in an appropriate cell culture medium (i.e., buffered sodium bicarbonate-free medium) in the absence of a $CO_2$-enriched environment, as specified, or unless cultured in DMEM, for which incubation was in 5% $CO_2$.

The adenoviral vectors employed in these experiments include the replication-deficient recombinant adenoviruses: Ad-CFTR, an Ad5-derived vector that possesses a deletion which encompasses all of the E1a region and part of the E1b and E3 regions, and contains a subcloned 4.5-kilobase human cystic fibrosis transmembrane conductance regulator (CFTR) cDNA driven by the Ad2 major later promoter (Rosenfeld et al., *Cell*, 68, 143–155 (1992)); and the E1a deletion virus Ad-dl312 (Jones et al., *Cell*, 17, 683–689 (1979)). The replication-competent Ad employed in these Examples was wild-type Ad5, which was obtained from H. Ginsberg of the Department of Microbiology, Columbia University. All viruses were propagated in 293 cells, recovered 36 hours after infection by 5 cycles of freezing/thawing, purified by CsCl density centrifugation (Graham et al., *Virology*, 52, 456–467 (1977)), dialyzed, and stored in virus dialysis buffer (10 mM Tris-HCl, pH 7.4, 1 mM $MgCl_2$, 10% glycerol) at −70° C. prior to use. Titers of the viral stocks were determined by plaque assay using 293 cells (Berkner, K. L., *BioTechniques*, 6, 606–629 (1988); Graham et al., *Virology*, 52, 456–467 (1977)). The plasmid vector pRSVL employed in cointernalization studies contains the Rous sarcoma virus long terminal repeat as a promoter driving expression of a reporter gene comprised of the firefly luciferase cDNA (de Wet et al., Mol. Cell Biol., 7, 725–37 (1987)).

For transfection of COS-7, HeLa, and CV-1 cells with pRSVL, exponentially growing cells were first detached using trypsin, and then seeded at a density of $1-2 \times 10^6$ cells in 10-cm diameter plates or, alternatively, a density of $0.5 \times 10^6$ cells in 60-mm diameter plates. After 20 hours, cells were washed once with a reduced serum medium (OPTI-MEM® I reduced serum medium; GIBCO/BRL, Grand Island, N.Y.), and were maintained in the OPTI-MEM® I medium for 2 hours until transfection. Unmodified pRSVL plasmid (typically 5 $\mu$g unless expressed otherwise) diluted in 0.1 ml of OPTI-MEM® I was then added directly to the cultured cells. After 0–30 minutes, either Ad-CFTR, Ad-dl312, or Ad5 (the amounts are stated with each experiment) was added to the plates and mixed in the cell culture medium by gentle rocking. The cultures were incubated for 24 hours. The medium was then aspirated and changed to DMEM supplemented with 10% FBS, or IMEM containing 10% fetal calf serum (FCS; Hyclone, Logan, Utah)), and the cells were incubated for another 24 hours. The cells were then scraped from the plates, washed twice with phosphate-buffered saline, pH 7.4 (PBS; BioWhittaker, Inc.), and evaluated for the amount of luciferase activity.

Luciferase activity in cultured cells was quantitated using standard methods (de Wet et al., Mol. Cell Biol., 7, 725–37 (1987)). After 48 hours incubation of cells with pRSVL (alone or in combination with Ad and/or liposomes), the cells were detached from the plates with trypsin, briefly pelleted, and washed twice with PBS. The cells were then resuspended in 150–200 $\mu$l of lysis buffer (100 mM potassium phosphate, pH 7.8 and 1 mM dithiothreitol (Sigma, St. Louis, Mo.), and lysed by 3 cycles of freezing and thawing. Cell lysates were obtained by centrifugation of the suspension at 15,000×g for 5 minutes at 4° C. Luciferase activity was assayed in a reaction incorporating 100 $\mu$l of cell lysate supernatant, 5 mM ATP (Pharmacia, Uppsala, Sweden) 15 mM $MgCl_2$, and 1 mM D-luciferin potassium, and using a Monolight 2010 luminometer (Analytical Luminescence Laboratories, San Diego, Calif.). The total protein concentration of the target cells was measured by the method of Bradford using a kit according to the recommendations of the manufacturer (Bradford, Anal. Biochem., 72, 248–254 (1975); Bio-Rad, Richmond, Calif.), and using bovine serum albumin as the standard. Luciferase activity was expressed as relative light units (RLU) per unit (either $\mu$g or mg) of cell lysate protein after subtracting background (de Wet et al., Mol. Cell Biol., 7, 725–37 (1987)).

In the present Example, cultures of COS-7 cells were exposed to amounts of pRSVL ranging from about 0–15 $\mu$g, either alone, or prior to infection with Ad-CFTR (200 plaque-forming units (PFU)/cell). Luciferase activity was monitored 48 hours later, and the average and standard error of the mean were calculated based on triplicate determinations.

As presented in FIG. 1, luciferase activity was observed at low levels in COS-7 cells after addition of pRSVL alone and increased about six-fold with increasing amounts of the plasmid. In contrast, COS-7 cells infected with Ad-CFTR following the addition of pRSVL demonstrated a substantial increase in luciferase activity. While pRSVL alone yielded a maximum of less than 15 RLU/$\mu$g of cell lysate protein, the addition of Ad-CFTR resulted in RLU/$\mu$g cell lysate protein values ranging from $10^4$ (using 0.1 $\mu$g of pRSVL) to $10^5$ (using 15 $\mu$g of pRSVL). This translates to a $10^4$-fold increase over the addition of the plasmid alone. Moreover, the results confirm that the adenovirus infection itself did not induce luciferase expression by the cells, since COS-7 cells infected with Ad-CFTR alone (in the absence of pRSVL) showed no luciferase activity.

The data in this Example validate that this strategy can be employed as a highly efficient method for transferring unmodified plasmid DNA into cultured cells in vitro. The present study, consistent with a number of studies with Ad-mediated cointernalization of proteins and carbohydrates (Ferná-Puentes et al., Cell, 20, 769–775 (1980); FitzGerald et al., Cell, 32, 607–617 (1983); Seth et al., Mol. Cell Biol., 4, 1528–1533 (1984); Yoshimura, Cell Struct. Funct., 10, 391–404 (1985); Otero et al., Virology, 160, 75–80 (1987); Defer et al., J. Virol., 64, 3661–3673 (1990); Carrasco, Virology, 113, 623–629 (1981); Yamaizumi et al., Virology, 95, 216–221 (1979); Carrasco et al., Virology, 117, 62–69 (1982)), demonstrates that plasmids, like other macromolecules, need not be coupled to the adenovirus or any other molecule for efficient cointernalization by Ad into target cells. Furthermore, the adenoviral-mediated augmentation of transfer and expression of plasmid-encoded DNA is dependent on the amount of the plasmid administered, with more transfection observed in accordance with greater amounts of plasmid administered.

EXAMPLE 2

The Adenoviral-Mediated Augmentation of Cell Transfection with pRSVL is Not Dependent on Use of a Particular Recipient Strain To determine whether Ad-mediated augmentation of transfection is a phenomenon specific to COS-7 cells or, more particularly, the SV40 components such as the SV40 large tumor antigen present within COS-7 cells, the cell lines HeLa and CV-1 (which do not produce SV40 components) were evaluated in parallel with COS-7 cells as set forth in Example 1. Transfections of each cell type were done in triplicate, and cells were infected with 200 PFU of Ad-CFTR/cell. After incubation, luciferase activity was measured in the cell lysate, corrected for total protein, and the mean of the triplicate samples for each condition was calculated. The -fold enhancement was calculated by dividing the mean of each condition by the mean of triplicates receiving pRSVL alone.

The results of these experiments presented in Table 2 (i.e., the first column) confirm the ability of Ad-CFTR to enhance luciferase activity in all three cell lines. The enhancement among the different cell types was in the range of 150- to 2000-fold, with CV-1 cells demonstrating the least enhancement, and COS-7 cells, the most.

TABLE 2

Comparison of adenovirus-mediated enhancement of luciferase activity among COS-7, HeLa and CV-1 cells transfected with pRSVL

| | Enhancement of luciferase activity | | |
|---|---|---|---|
| Cell Line | Ad-CFTR alone -fold | Cationic liposomes alone -fold | Ad-CFTR plus cationic liposomes -fold |
| COS-7 | $2.1 \times 10^3$ | $1.5 \times 10^4$ | $1.1 \times 10^5$ |
| HeLa | $1.8 \times 10^3$ | $2.0 \times 10^5$ | $1.2 \times 10^6$ |
| CV-1 | $1.4 \times 10^2$ | $4.5 \times 10^3$ | $9.3 \times 10^3$ |

These results confirm that Ad-mediated augmentation of cell transfection can be obtained using different types of eukaryotic cells. It cannot be discerned from these data whether the greater degree of augmentation in SV40-transformed COS-7 cells as compared with CV-1 cells is due to an interaction of the adenovirus with the SV40 component of the COS-7 cells. However, since HeLa cells (which, like CV-1 cells, do not produce SV40 components) show similar to greater enhancement as compared with the COS-7 cells, these results confirm that the adenoviral-mediated enhancement of cell transfection is not dependent on an interaction specific to SV40-transformed cells, and can be observed in other eukaryotic cells.

EXAMPLE 3

The Adenoviral-Mediated Augmentation of Cell Transfection with pRSVL is Not Dependent on the Use of a Particular Adenoviral Vector To determine whether Ad-mediated augmentation of transfection is a phenomenon specific to the Ad-CFTR vector, the Ad5 and Ad-dl312 vectors were evaluated in parallel with Ad-CFTR as set forth in Example 1. Transfections of COS-7 cells were done in triplicate, and the average and standard error of the mean were based on these triplicate determinations.

Figure 2:
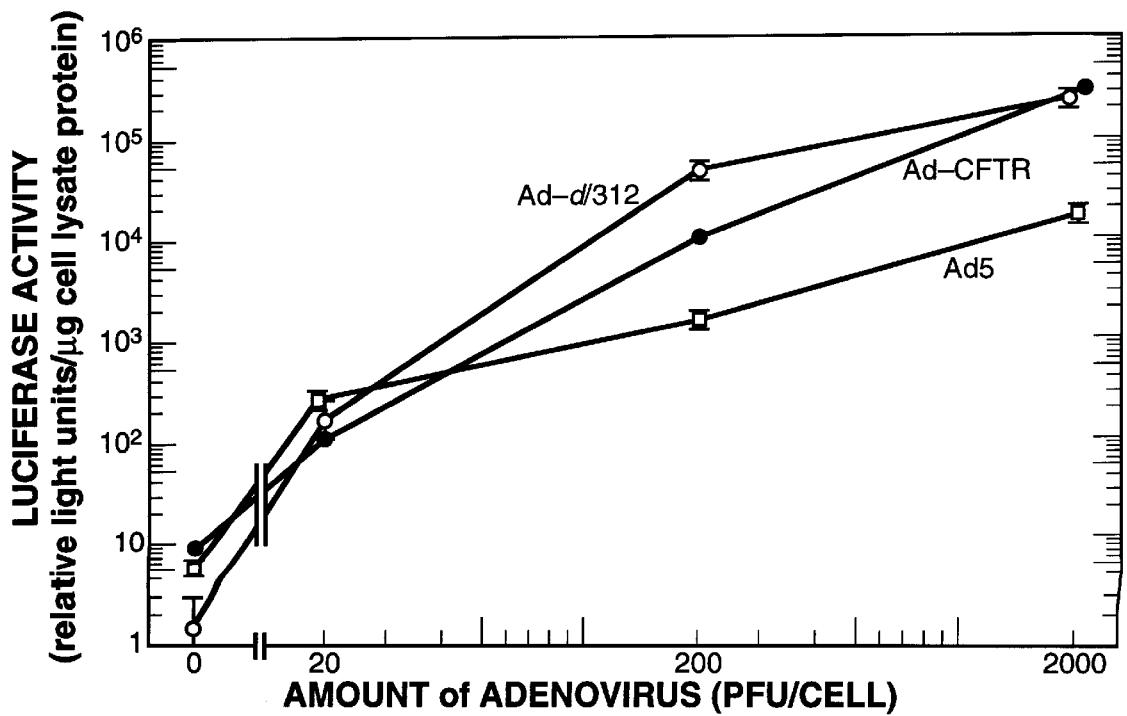
FIG. 2 is a graph of adenovirus amount ($\mu$g) versus luciferase activity (RLU/$\mu$g cell lysate protein) for COS-7 cells incubated with pRSVL and increasing amounts of Ad-CFTR ($\bullet$), Ad-5 ($\square$) or Ad-dl312 ($\circ$).

The results presented in FIG. 2 confirm that the augmentation of expression of the luciferase gene is not specific to Ad-CFTR, and is not mediated by the exogenous cystic fibrosis transmembrane conductance regulator (CFTR) cDNA contained in Ad-CFTR, since augmentation was observed with other adenoviruses not incorporating the CFTR cDNA, including the E1a deletion mutant Ad-dl312, and wild-type Ad5.

To investigate a dose-response relationship between the amount of Ad administered and luciferase activity, 0–2000 PFU/cell of Ad-CFTR, Ad-dl312, or Ad5 were added to the COS-7 cells exposed to 15 μg of pRSVL. For all three adenoviral vectors, the augmentation of the expression of the plasmid vector-encoded luciferase reporter gene in COS-7 cells was observed in a dose-dependent fashion. When no Ad was added, the COS-7 cells exhibited base-line luciferase activity (i.e., as demonstrated by the line labelled pRSVL plasmid 'Alone' in FIG. 1). However, when increasing amounts of Ad ranging from 20 to 200 PFU/cell were added, luciferase activity increased correspondingly. COS-7 cells infected with 2000 PFU/cell of each Ad demonstrated luciferase activity that was $10^4$-fold higher than when no Ad was added, regardless of which Ad was used in the study.

These results validate that Ad-mediated augmentation of cell transfection can be obtained using different types of Ad, and more particularly, using either replication-deficient or -competent adenoviruses. Since a similar level of enhancement of transfer and expression of the foreign gene in the plasmid can be achieved with a replication-deficient recombinant Ad as with wild-type Ad, a replication-deficient recombinant Ad can be employed instead of wild-type Ad, thus eliminating harmful adverse effects of infection with wild-type Ad, such as cell death. Moreover, the effect of the Ad augmenting transfer and expression of the gene within plasmid DNA is dependent on the amount of Ad administered.

EXAMPLE 4

Adenoviral-Mediated Augmentation of Cell Transfection with pRSVL can be Further Increased when Cells are Exposed to pRSVL Preincubated with Cationic Liposomes To enable a comparison of the efficiency of Ad-mediated augmentation of cell transfection with transfection effected by a known transfection reagent, expression of the luciferase reporter gene in COS-7 cells exposed to the pRSVL plasmid together with cationic liposomes was evaluated along with cells exposed to pRSVL plus cationic liposomes followed by Ad-CFTR infection (200 PFU/cell).

The cationic liposomes employed in this Example were obtained using Lipofectin® Reagent (Bethesda Research Laboratories), which comprises positively charged N-[1-(2, 3-dioleyloxy)propyl]-N,N,N-trimethylammonium chloride (DOTMA) liposomes. It has been previously demonstrated (Felgner et al., Proc. Natl. Acad. Sci., 84, 7413–7417 (1987)) and is presented in FIG. 3 that exposure of cells (such as the COS-7 cells employed in this Example) to cationic liposomes mixed with a plasmid (in this case, pRSVL) augments transfection of COS-7 cells in a dose-dependent fashion. For these experiments, amounts of liposomes ranging from 0–100 μg were mixed with 15 μg of pRSVL in a total volume of 100 μl according to the liposome manufacturer's protocol, and the resultant liposome-DNA complexes were added to COS-7 cells. Cells were evaluated for luciferase activity after 48 hours of transfection in the absence or presence of infection with 200 PFU/cell of Ad-CFTR, and the average and standard error of the mean were calculated based on triplicate determinations.

Figure 3:
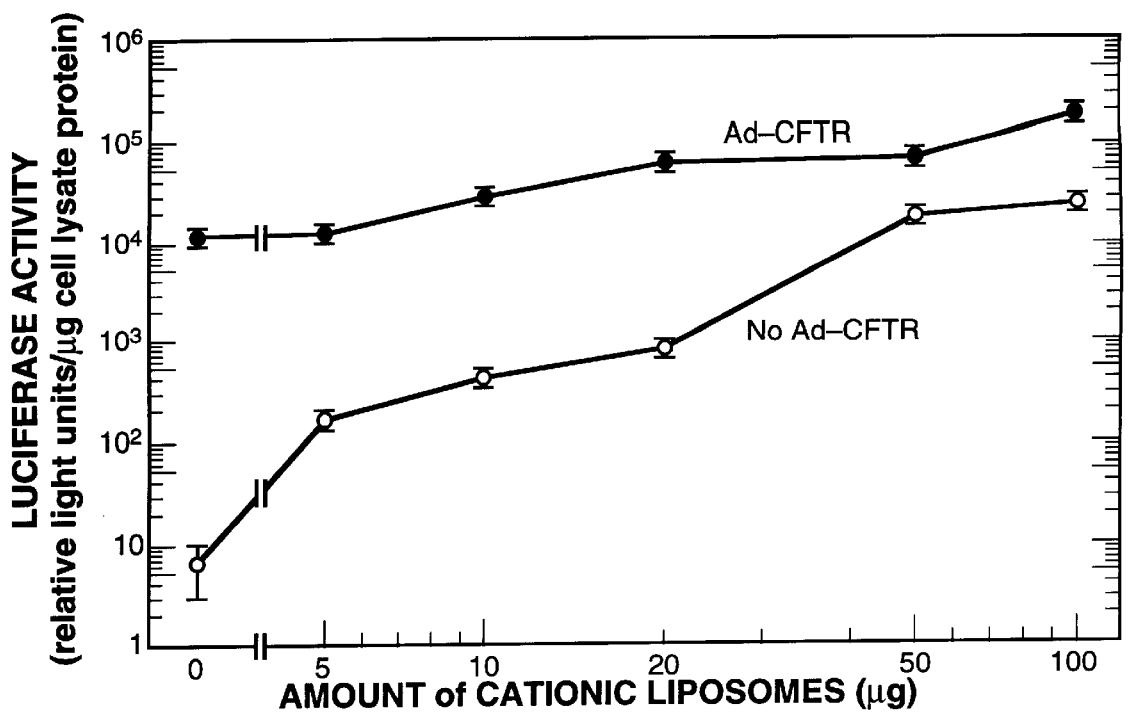
FIG. 3 is a graph of amount of cationic liposomes ($\mu$g) versus luciferase activity (RLU/$\mu$g cell lysate protein) for COS-7 cells incubated with pRSVL and increasing amounts of cationic liposomes in the absence of ($\circ$) or prior to ($\bullet$) infection with Ad-CFTR.

As presented in FIG. 3, increasing amounts of liposomes added to the cells along with a fixed amount of pRSVL resulted in an increase in luciferase activity in COS-7 cells from a basal level (corresponding to the addition of no liposomes), to a level of $10^4$ RLU/μg cell lysate protein (corresponding to the addition of 50 or 100 μg of cationic liposomes). Cells incubated with liposomes alone did not demonstrate luciferase activity (data not shown).

The level of luciferase activity obtained upon transfection with pRSVL preincubated with 50 μg of liposomes (e.g., FIG. 3 and Table 2, last two columns) was similar to the level of luciferase activity obtained by Ad-CFTR infection plus pRSVL (e.g., FIG. 2). However, when Ad-CFTR infection was employed subsequent to exposure of the cells to the liposomes plus DNA, an even greater enhancement of reporter gene expression was obtained than upon exposure of the cells to pRSVL with either liposomes or Ad-CFTR alone, as presented in FIG. 3 and Table 2 (last two columns). This synergistic augmentation ranged from 4- to 100-fold (depending on the amount of liposomes added), and demonstrated dose-responsiveness, with increasing luciferase activity obtained with use of increasing amounts of cationic liposomes.

The synergistic augmentation of adenoviral-mediated cell transfection when plasmid DNA is preincubated with cationic liposomes is observed not only in COS-7 cells, but is obtained in HeLa and CV-1 cells as well. For these experiments, COS-7, HeLa, and CV-1 cells evaluated in parallel were transfected with 15 μg of pRSVL in the presence or absence of liposomes (50 μg) and Ad-CFTR (200 PFU/cell). Transfections were done in triplicate for each condition. As presented in Table 2, the synergistic enhancement observed for the three cell types ranged from $10^4$- to $10^6$-fold, with HeLa cells demonstrating the greatest enhancement, and CV-1 cells, the least.

This Example confirms that the efficiency of the Ad-mediated augmentation of cell transfection with an unmodified plasmid vector is comparable with that obtained by transfection with liposome-DNA complexes. Further, the results confirm that the two phenomena can act synergistically to enhance transfer and expression of a reporter gene contained within the plasmid.

EXAMPLE 5

Adenoviral-Mediated Augmentation of Cell Transfection with pRSVL Requires RME in the Target Cell In this Example, the ability of Ad-CFTR to augment cell transfection subsequent to binding of Ad-CFTR to the cell surface was investigated.

COS-7 cells were incubated with different concentrations of Ad-CFTR at 4° C. for 4 h to prevent RME. Since this incubation was done under atmospheric conditions, cells were incubated in sodium bicarbonate-free IMEM containing 20 mM N'-2-hydroxyethylpiperazine-N'-2-ethanesulfonic acid (HEPES, pH 7.5, Sigma), which medium does not require exogenous $CO_2$ as a means of controlling pH. At the end of the incubation, unbound virus particles were washed from the monolayers with Opti-MEM® I. The culture temperature was then raised to 37° C., and plasmid pRSVL (5 μg) was added to the cell culture. After 48 hours, luciferase activity in the cell lysate was determined as described in Example 1. The average and standard error of the mean were calculated based on triplicate determinations.

Figure 4:
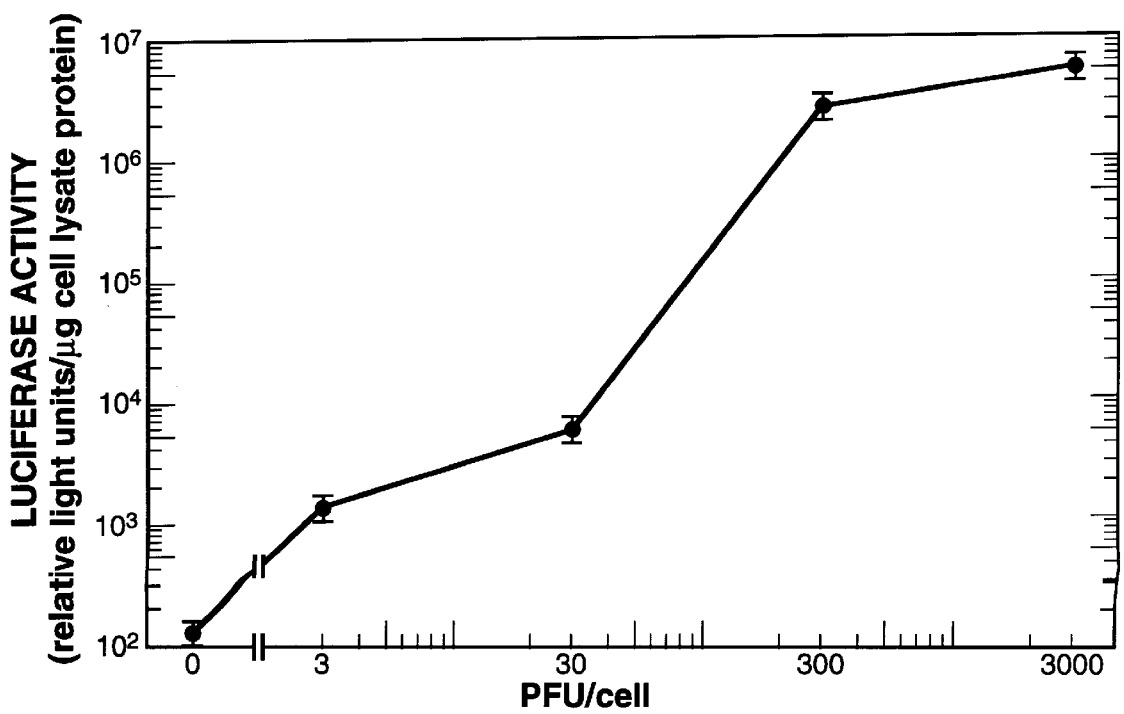
FIG. 4 is a graph of Ad-CFTR amount ($\mu$g) versus luciferase activity (RLU/mg cell lysate protein) for COS-7 cells incubated with increasing amounts of Ad-CFTR at 4° C. for 4 hours, after which the temperature was raised to 37° C. and the plasmid pRSVL was added.

The ability of Ad-CFTR bound to a cell surface receptor to mediate the increase in the expression of pRSVL in COS-7 cells is presented in FIG. 4. In the absence of Ad-CFTR, cells exposed to plasmid pRSVL alone exhibited low levels of luciferase activity ($2.5 \times 10^2$ RLU/mg of protein). Increasing the concentration of Ad-CFTR resulted in a corresponding increase in the expression of the plasmid, with the highest concentration of Ad-CFTR (15 μg/ml) yielding $8 \times 10^6$ RLU/mg of protein, which constitutes a $3 \times 10^4$-fold increase in luciferase activity compared with addition of the plasmid alone.

This study confirms that the process of replication-deficient adenovirus-mediated enhancement of plasmid DNA transfer and subsequent expression in cells requires RME in the target cell. When the replication-deficient vector was bound to the cell surface and the excess virus particles were washed away, the vector was still able to transfect DNA into the cells. This most likely could take place only if the virus particles were tightly bound to the cell surface (presumably to the virus receptor), and both the vector and plasmid DNA were subsequently cointernalized.

EXAMPLE 6

Adenoviral-Mediated Augmentation of Cell Transfection with pRSVL is Effected Through Interaction with the Adenoviral Receptor, and, More Particularly, with the Ad Fiber In this experiment, the specific role of the adenovirus receptor in the cointernalization process was further clarified by evaluating the ability of Ad5 fiber protein to block the Ad-CFTR-dependent increase in pRSVL expression.

Adenovirus proteins were purified by isolating from the Ad5 genome through use of the polymerase chain reaction a cDNA clone of the Ad5 gene encoding the fiber protein. The fiber protein cDNA was subcloned into a pMAL vector (New England Biolabs, Beverly, Mass.), allowing the fiber protein to be expressed as a fusion protein and purified by affinity chromatography, as specified by the manufacturer. Additionally, fiber and hexon were purified from Ad-CFTR-infected 293 cells as previously described (Boulanger et al., Eur. J. Biochem., 39, 37–42 (1973)), except that DEAE-Bio-Gel (Bio-Rad) was used for the ion-exchange chromatography step, and the proteins were further purified through an additional affinity chromatography step using antiserum directed against Ad-CFTR bound to an Affi-Gel-Hz column (Bio-Rad). The Ad-CFTR antiserum was produced in rabbits as previously described for Ad2 (Seth et al., Mol. Cell. Biol., 4, 1528–1533 (1984)). Fiber was eluted from the column with 4M sodium thiocyanate (Sigma).

COS-7 cells were exposed to Ad-CFTR (10 PFU/cell) and plasmid pRSVL (5 μg) in the presence of increasing concentrations of either fiber or hexon for 24 hours, following which luciferase activity was determined. The value for RLU/mg of cell lysate protein in control cells which were not exposed to fiber or hexon was considered to represent 100% activity, and the luciferase activity observed in the presence of fiber or hexon was calculated relative to this control value. The average and standard error of the mean were calculated based on triplicate determinations.

Figure 5:
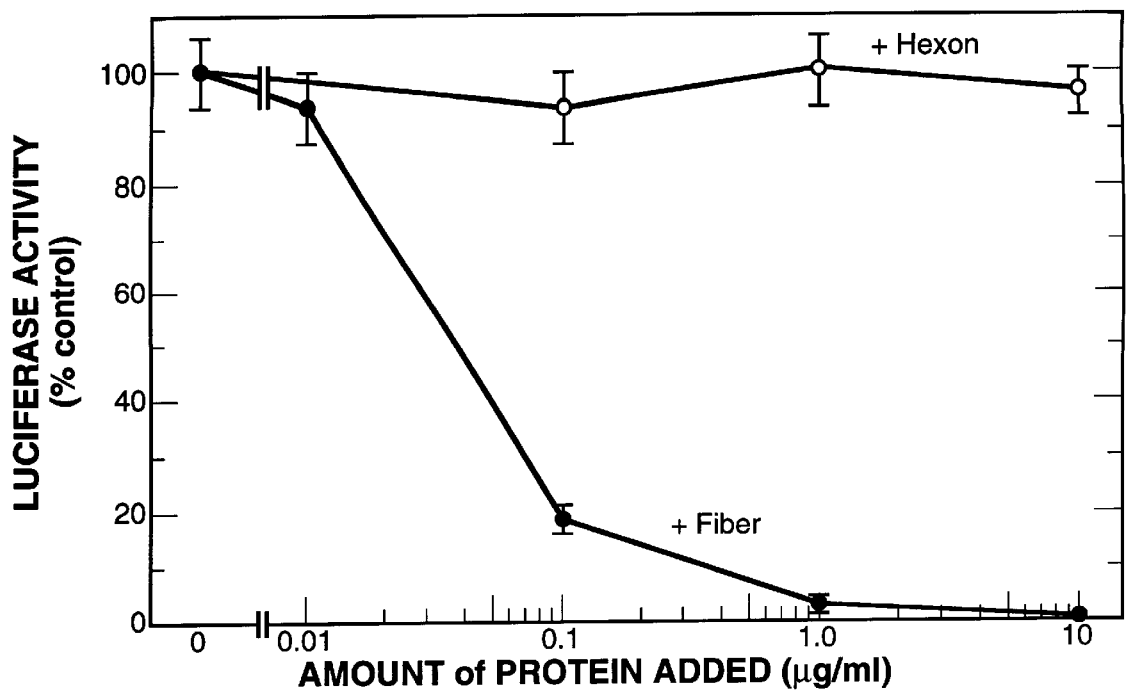
FIG. 5 is a graph of amount of protein added ($\mu$g/ml) versus luciferase activity (% control) for COS-7 cells incubated with Ad-CFTR and pRSVL in the presence of increasing amounts of fiber ($\bullet$) or hexon ($\circ$).

As presented in FIG. 5, COS-7 cells exposed to Ad-CFTR and pRSVL in the presence of different concentrations of fiber purified from Ad-CFTR-infected 293 cells exhibited a dose-dependent inhibition of the ability of Ad-CFTR to increase the expression of the plasmid. For example, addition of 0.1 μg/ml of pure fiber resulted in greater than 90% inhibition of Ad-CFTR-mediated pRSVL expression. Similar results were obtained for fiber purified using the expression vector pMAL (data not shown). Additionally, fiber was also able to prevent labeled Ad-CFTR from binding to the cell surface at 4° C. (data not shown). The specificity of the inhibitory effects of fiber was confirmed by adding increasing amounts of the adenovirus hexon protein. Whereas adenovirus fiber was able to compete with the transfection-enhancing effects of the vector, hexon failed to exhibit such inhibitory effects.

These results indicate that binding of the vector to the cell receptor through the fiber protein is critical for the vector-mediated internalization process, and supports that the process of adenoviral-mediated enhancement of DNA transfer to target cells requires RME in the target cell.

EXAMPLE 7

Adenoviral-Mediated Augmentation of Cell Transfection with pRSVL is Dependent on the Adenoviral Receptor and Correlates with the Number of Receptors Present on a Particular Cell Type In this experiment, the specific role of the adenovirus receptor in the cointernalization process was further clarified by correlating differences in Ad-mediated augmentation of DNA transfer among different cell types with the number and kinetic parameters of Ad receptors present on the cell surface.

Receptor number and kinetic parameters of Ad-CFTR binding were investigated in four different cell lines (COS-7, HeLa, U-937, and NIH 3T3) in parallel with a comparative study of the ability of Ad-CFTR to increase pRSVL expression in these different target cells. The U-937 cell line is a human histiocytic lymphoma cell line (ATCC CRL 1593), and the NIH 3T3 cell line is a Swiss mouse embryo cell line (ATCC CRL 1658). Cell cultures were grown as monolayers in IMEM supplemented with 10% CS, 50 units/ml penicillin, and 50 μg/ml streptomycin (all from Biofluids).

To carry out the analysis of Ad-CFTR receptor number and kinetic parameters, Ad-CFTR was metabolically labeled in 293 cells as previously described (Seth et al., Mol. Cell. Biol., 4, 1528–1533 (1984); Seth et al., J. Virol., 51, 650–655 (1984)), with slight modifications. 293 cells were seeded in 150-mm diameter plates at a density of about $4 \times 10^6$ cells/plate, and the cells were infected 24 hours later with Ad-CFTR (100 PFU/cell; diluted in IMEM containing 2% CS). Following a 2 hour incubation, the medium was changed to IMEM supplemented with 10% serum. After 10 hours, the medium was changed to methionine-free IMEM containing 2% dialyzed CS (Gibco/BRL), 1% CS, and [$^{35}$S]methionine (100 μCi/ml; >1,000 μCi/mmol; Amersham, Arlington Heights, Ill.). After 12 hours, the infected cells were harvested and [$^{35}$S]Ad-CFTR was purified as described previously for Ad-CFTR (Rosenfeld et al., Cell, 68, 143–155 (1992)).

To measure binding of [$^{35}$S]Ad-CFTR to various cells, cells were seeded in 12-well plates at a density of $10^5$ cells/plate. After incubation for 24 hours, the cells were washed with sodium bicarbonate-free IMEM containing 20 mM HEPES (pH 7.5), and were incubated with 0.2 μg of [$^{35}$S]Ad-CFTR (specific activity, $10^6$ dpm/μg of protein) in the same medium at 4° C. for 2 hours. The cells were then washed four times with PBS, and were then suspended in 0.2 ml of 0.1N NaOH. The radioactivity present in each sample was quantified by scintillation counting.

Scatchard plot analysis of [$^{35}$S]Ad-CFTR binding to cells was performed in the presence of different concentrations of unlabeled Ad-CFTR (up to 200 μg of protein). For each concentration of virus, values of free and bound Ad-CFTR were calculated, and Scatchard plots were used to calculate the receptor number and the affinity constants of Ad-CFTR binding to cells (Scatchard, Ann. N.Y. Acad. Sci., 51, 660–672 (1949)).

Figure 6:
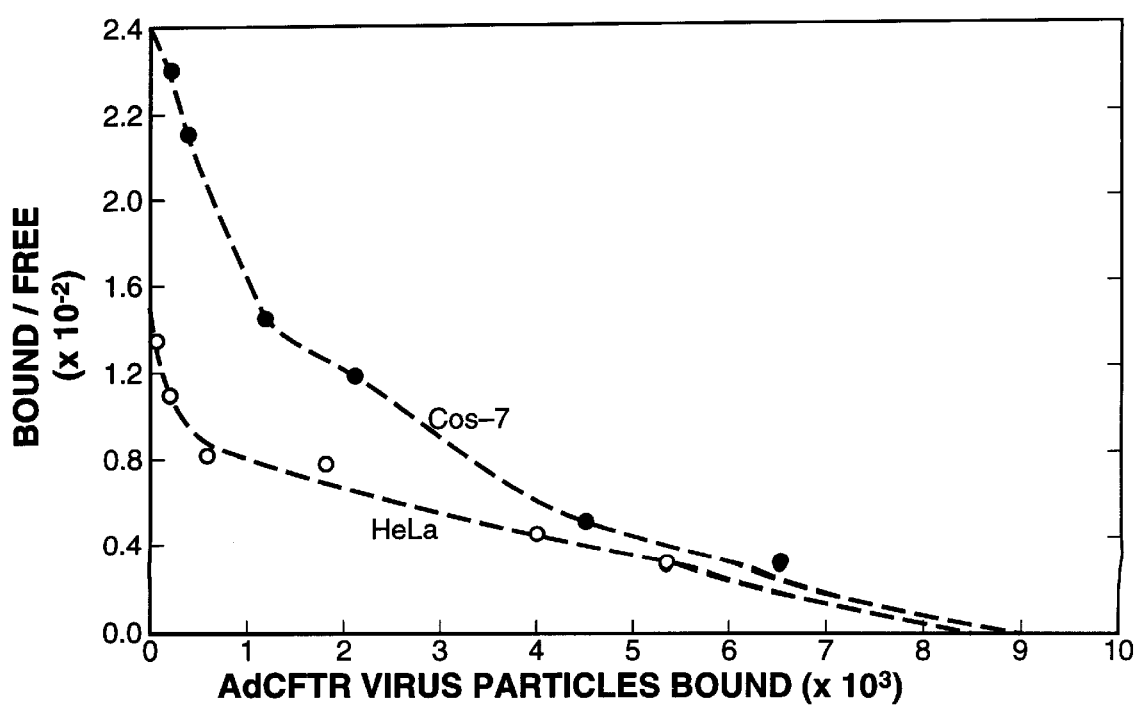
FIG. 6 is a graph of amount of Ad-CFTR virus particles bound ($\times 10^3$) versus bound/free ($\times 10^{-2}$) for COS-7 ($\bullet$) or HeLa ($\circ$) cells incubated with increasing concentrations of [$^{35}$S]Ad-CFTR for 2 hours at 4° C.

As presented in FIG. 6, and as previously described for HeLa cells (Persson et al., J. Virol., 54, 92–97 (1985)), COS-7 and HeLa cells appear to possess both high-affinity and low-affinity receptors. Further, as indicated in Table 3, for COS-7 and HeLa cells, the number of low affinity receptors was in the range of $8\times10^3$ to $9\times10^3$ receptors/cell, and the number of high affinity receptors was in the range of $9\times10^2$ to $2.5\times10^3$ receptors/cell. Consistent with the presence of Ad-CFTR receptors on these two cell lines, both demonstrated an Ad-CFTR-mediated increase in the expression of pRSVL, with the observed increase greater than 800-fold for COS-7 cells, and greater than 500-fold for HeLa cells. In contrast, under the comparable conditions, U-937 and NIH 3T3 cells exhibited a low number of receptors specific for Ad-CFTR (i.e., less than 100 high affinity receptors/cell, and less than $1\times10^3$ low affinity receptors/cell), and the Ad-CFTR-mediated increase in expression of pRSVL was substantially less than that observed in COS-7 and HeLa cells (i.e., reaching only between 1.6 or 3.1 fold).

TABLE 3

Comparison of the increase in luciferase expression modulated by the cointernalization of a replication-deficient adenovirus and a plasmid containing the luciferase cDNA with the number of receptors for the adenovirus on the surface of various cell types.

| Cell line | Luciferase activity (fold increase in the presence of Ad-CFTR) | Number of Ad-CFTR receptors | |
|---|---|---|---|
| | | High affinity | Low affinity |
| COS-7 | 827 | 2,787 | 9,175 |
| HeLa | 550 | 1,325 | 8,376 |
| NIH 3T3 | 3.1 | <100 | <1,000 |
| U-937 | 1.6 | <100 | <1,000 |

These results confirm the strong correlation between the number of adenovirus receptors on the cell surface and the relative efficiency of the adenovirus-mediated enhancement of plasmid DNA expression in target cells. The results thus further validate a specific role of the adenovirus receptor in the cointernalization of plasmid DNA. Moreover, since many cell lines routinely used for transfection studies possess adenovirus receptors, as must many cells in vivo (as evidenced by the ubiquity of adenoviral infection), the results confirm the broad utility of present approach for RME of cointernalized plasmid both in vitro and in vivo.

EXAMPLE 8

Adenoviral-Mediated Augmentation of Cell Transfection with pRSVL Requires Disruption of the Endocytic Vesicle Following Cointernalization of the Plasmid with the Adenovirus To clarify understanding and thus utilization of the present invention, the mechanism underlying adenoviral-mediated augmentation of cell transfection was further investigated. In this Example, the importance of Ad-CFTR-dependent disruption of endocytic vesicles following cointernalization of Ad-CFTR and plasmid pRSVL was investigated by evaluating the effect on the Ad-CFTR-mediated increase in plasmid DNA expression of inhibition of Ad-CFTR-dependent lysis of endocytic vesicles in the absence of any substantial effect on the uptake of adenovirus into the cells.

Three such conditions were tested for their effects on Ad-CFTR-dependent increase in plasmid luciferase expression and uptake of [$^{35}$S]Ad-CFTR into cells: (1) heat treatment of Ad-CFTR at 45° C.; (2) treatment of Ad-CFTR with low concentrations of Ad-CFTR antiserum; and (3) treatment of target cells with chloroquine, an agent known to raise the pH of the endocytic vesicles.

For these experiments, Ad-CFTR was metabolically labeled as described in Example 7. The uptake of [$^{35}$S]Ad-CFTR into cells was evaluated as previously described for uptake of [$^{35}$S]Ad2 (Seth et al., J. Virol., 51, 650–655 (1984)). In other words, the cells were exposed to 0.1 μg of [$^{35}$S]Ad-CFTR (specific activity, $10^6$ dpm/μg) and appropriate amounts of unlabeled Ad-CFTR as described above and incubated at 37° C. for 1 hour. The cells were then washed three times with PBS and treated with 0.5 ml of trypsin for 15 minutes at 37° C. to remove membrane-bound virus. The cells were then suspended in 0.2 ml of 0.1N NaOH, and radioactivity was measured in a scintillation counter to estimate the amount of virus taken up by cells.

To evaluate the effect of temperature on the ability of Ad-CFTR to mediate cointernalization of plasmid pRSVL, Ad-CFTR was incubated at different temperatures for 15 minutes in a buffer containing 10% glycerol and 20 mM Tris (pH 7.5). The virus preparations were then cooled at 4° C. for 10 minutes, and were then added to COS-7 cells along with plasmid pRSVL. Luciferase activity was determined after 48 hours. In parallel cultures, [$^{35}$S]Ad-CFTR was added to appropriate amounts of unlabeled Ad-CFTR, and uptake of the labeled vector was determined as described above. Luciferase activity and the amount of $^{35}$S-labeled Ad-CFTR taken up in the cells when Ad-CFTR was preincubated at 4° C. were considered 100%, and the mean and standard error of the mean were calculated based on triplicate determinations.

The integrity of Ad-CFTR following heat treatment was confirmed by centrifuging the virus preparations incubated at different temperatures at 100,000×g for 30 minutes, and then analyzing the composition of the viral proteins in the pellets was by sodium dodecyl sulfate (SDS)-gel electrophoresis. Disappearance of viral proteins from the pellets indicated disruption of Ad-CFTR as a consequence of a particular treatment condition.

Figure 7:
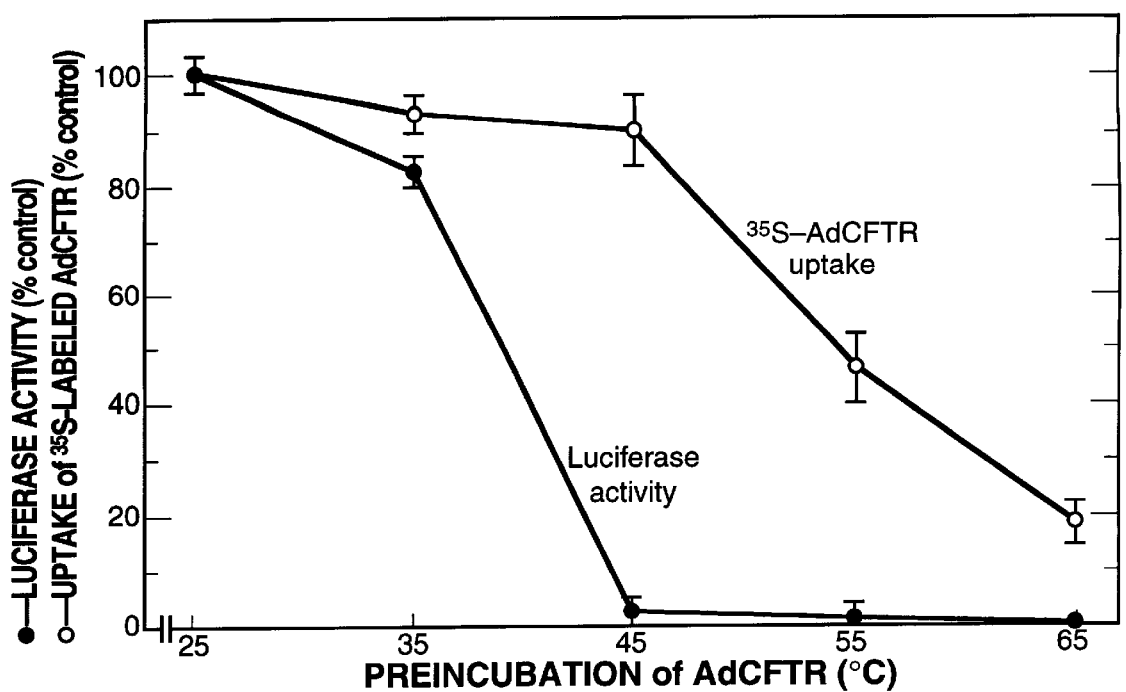
FIG. 7 is a graph of preincubation temperature of Ad-CFTR (°C.) versus luciferase activity on the left ordinate (% control; $\bullet$) and uptake of labeled Ad-CFTR on the right ordinate (% control; $\circ$) for COS-7 cells incubated with pRSVL prior to infection with heat-treated Ad-CFTR ($\bullet$) or with heat-treated Ad-CFTR and labeled Ad-CFTR ($\circ$).

As presented in FIG. 7, incubation of the virus at 25° C. did not significantly affect either the Ad-CFTR-dependent increase in luciferase expression or the uptake of the virus into cells. Following virus incubation at 35° C., about a 20% loss in the Ad-CFTR-dependent luciferase activity was observed, and less than a 5% loss in the uptake of virus into the cells. Following incubation at 45° C., greater than a 95% loss in the Ad-CFTR-dependent luciferase activity was observed, and was accompanied by a 15% loss in the uptake of Ad-CFTR into cells. In comparison, following incubation of the virus at 55° C., greater than a 95% loss in the Ad-CFTR-dependent luciferase activity was observed, and the decline in Ad-CFTR uptake was about 50%. It is conceivable that following pretreatment of virus at 55° C., there is an incomplete dissociation of Ad-CFTR uptake and Ad-CFTR-mediated plasmid transfer. This would suggest that heating virus for a longer period of time or in a different buffer (for example, a buffer devoid of glycerol) might completely destroy virus uptake as well as the ability of the virus to enhance plasmid transfer and expression. In fact, temperatures of 65° C. or above resulted in abolition of most of the Ad-CFTR-induced enhancement of the uptake and expression of the plasmid, likely because of loss of virus uptake into target cells.

The integrity of Ad-CFTR following exposure to different temperatures was investigated to further explain the effects of Ad-CFTR heat treatment on the adenoviral-mediated increase in plasmid expression. While the protein composition of Ad-CFTR was apparently not altered by heat treatment at 25, 37 and 45° C., following treatment at 55 and 65° C., about 60 to 70% of the viral proteins disappeared from Ad-CFTR (data not shown). These results suggest that Ad-CFTR remained completely intact after heating at up to 45° C. while higher temperatures resulted in disruption of viral integrity.

The effect of Ad-CFTR antiserum on Ad-CFTR-dependent pRSVL expression was investigated by mixing Ad-CFTR with various concentrations of Ad-CFTR antiserum at room temperature for 15 minutes, and exposing to COS-7 cells in the presence of plasmid pRSVL. Following a 48 hour incubation, luciferase activities were determined. In parallel experiments, [$^{35}$S]Ad-CFTR mixed with unlabeled Ad-CFTR was incubated with Ad-CFTR antiserum for 15 minutes at room temperature and exposed to COS-7 cells for 1 hour at 37° C. After trypsinization of cells for 15 minutes to remove surface-bound labeled virus, the amount of [$^{35}$S]Ad-CFTR internalized into the cells was determined by counting the cell-associated radioactivity. The luciferase activities and amounts of [$^{35}$S]Ad-CFTR internalized by cells was graphed relative to values obtained for Ad-CFTR or [$^{35}$S]Ad-CFTR not exposed to the antiserum.

Figure 8:
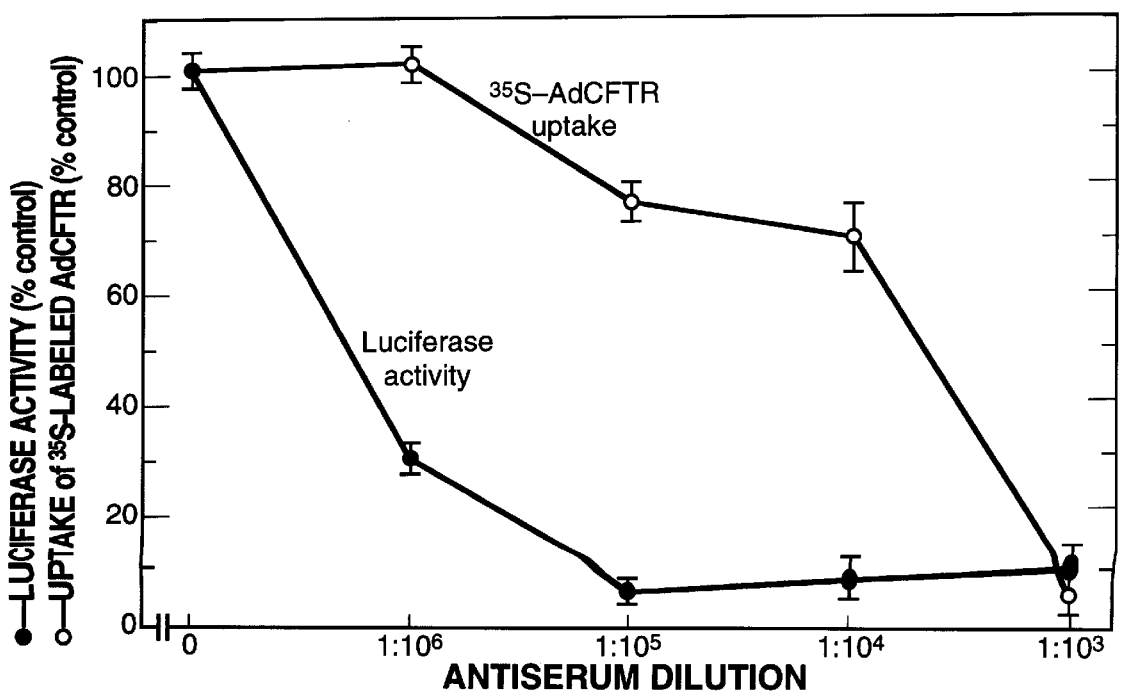
FIG. 8 is a graph of antiserum dilution versus luciferase activity on the left ordinate (% control; $\circ$) and uptake of labeled Ad-CFTR on the right ordinate (% control; $\circ$) for COS-7 cells incubated with pRSVL prior to infection with Ad-CFTR that had been preincubated with the antiserum for 15 minutes at room temperature ($\bullet$) or with Ad-CFTR that had been preincubated with the antiserum for 15 minutes at room temperature and with labeled Ad-CFTR ($\circ$).

As presented in FIG. 8, when Ad-CFTR was incubated with increasing concentrations of Ad-CFTR antiserum, a corresponding decline in the Ad-CFTR-dependent increase in luciferase expression was observed. Following incubation with an antiserum dilution of 1:10$^6$, the adenovirus-mediated increase in luciferase activity was inhibited by 75%, while the uptake of Ad-CFTR into cells was not affected. Following incubation with an antiserum dilution of 1:10$^5$, the adenovirus-mediated increase in luciferase expression was inhibited by more than 90%, while the uptake of [$^{35}$S]Ad-CFTR into the cells was inhibited by only about 25%. Furthermore, following incubation with an antiserum dilution of 1:10$^4$, incomplete dissociation of Ad-CFTR uptake and Ad-CFTR-mediated plasmid transfer was still observed, with the obtained luciferase activity and uptake values approximating those obtained for treatment of Ad-CFTR with an antiserum dilution of 1:10$^5$. However, following treatment of Ad-CFTR with antiserum dilutions of 1:10$^3$ (or lesser dilutions; data not shown), greater than a 90% loss of both the Ad-CFTR-dependent increase in luciferase activity and the ability of the vector to enter the cells was observed.

In view of the fact that the agent chloroquine prevents adenovirus from disrupting endosomes (Seth et al., *J. Virol.*, 51, 650–655 (1984)), the ability of chloroquine (Sigma) to prevent the Ad-CFTR-mediated increase in the expression of the luciferase plasmid was evaluated. In this set of experiments, COS-7 cells were exposed to Ad-CFTR in the presence of plasmid pRSVL and concentrations of chloroquine ranging from 0 to 200 $\mu$M. After 24 hours the medium was changed, the cells were incubated for another 24 hours, and luciferase activities were determined. In parallel cultures, COS-7 cells were exposed to [$^{35}$S]Ad-CFTR in the presence of various concentrations of chloroquine for 1 hour, and the amount of [$^{35}$S]Ad-CFTR taken up into the cells was determined. Luciferase activity and the amount of $^{35}$S-labeled Ad-CFTR taken up in the cells which did not receive chloroquine were considered 100%. Control cells received chloroquine and pRSVL alone, and the luciferase activity obtained in these cells was subtracted from the activity of cells that received pRSVL along with Ad-CFTR and chloroquine.

Figure 9:
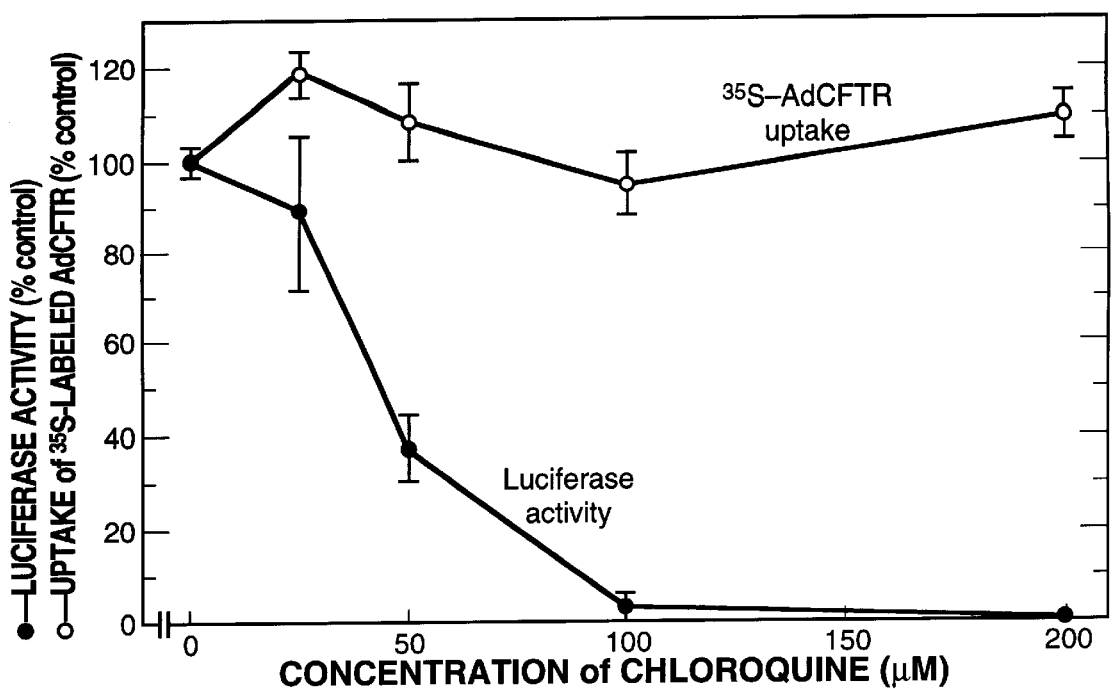
FIG. 9 is a graph of chloroquine concentration ($\mu$M) versus luciferase activity on the left ordinate (% control; $\bullet$) and uptake of labeled Ad-CFTR on the right ordinate (% control; $\circ$) for COS-7 cells exposed to pRSVL, the indicated concentrations of chloroquine and either Ad-CFTR ($\bullet$) or Ad-CFTR mixed with labeled Ad-CFTR ($\circ$).

As presented in FIG. 9, treatment of cells with increasing concentrations of chloroquine effected a corresponding loss in Ad-CFTR-dependent luciferase expression. In contrast, treatment of control cells with chloroquine resulted in a slight increase (i.e., about 1.5-fold) in the expression of pRSVL (data not shown). The chloroquine inhibitory effect was concentration dependent, and 50% inhibition was observed with a chloroquine concentration of less than 50 $\mu$M. Under these conditions, uptake of [$^{35}$S]Ad-CFTR into cells was not inhibited.

These results confirm a requirement for adenoviral-dependent lysis of the endocytic vesicle for observation of adenovirus-mediated cointernalization of plasmid. Three conditions known to block the release of adenovirus from the endocytic vesicle also inhibited the adenoviral-mediated increase in plasmid DNA expression in target cells, i.e.: (1) heat treatment of Ad-CFTR at 45° C.; (2) treatment of Ad-CFTR with low concentrations of Ad-CFTR antiserum; and (3) treatment of target cells with chloroquine, an agent known to raise the pH of the endocytic vesicles. None of these conditions substantially prevented the entry of the adenovirus vector into the cells. Further, Ad-CFTR appeared to be completely intact following heat treatment at 45° C. These results validate that vector-dependent lysis of endocytic vesicles is necessary for the release of plasmid DNA from the endocytic vesicles, and that the low-pH environment of endocytic vesicles is critical for this process. Moreover, the ability to dissociate the binding and endosomal lysis properties of adenovirus suggests that the present invention could be further manipulated to construct recombinant adenoviral vectors which combine the cell or tissue specificities of different viruses with the endosomal lysis and nuclear transport capabilities of adenovirus.

EXAMPLE 9

Adenoviral-Mediated Augmentation of Cell Transfection with pRSVL is not Dependent on the Adenoviral Genome In this Example, the necessity of the adenoviral genome for observation of the Ad-CFTR-mediated increase in transfer and expression of plasmid pRSVL in host cells was evaluated.

To assess the effect of inactivation of the viral genome by UV radiation on the Ad-CFTR-dependent increase in expression of the luciferase plasmid, Ad-CFTR was irradiated at a distance of 6 cm for various lengths of time using a short-wavelength UV lamp (Model UV G-54; UVP, Inc., San Gabriel, Calif.). The irradiated preparation was then evaluated for the ability of the viral genome to usurp host cell functions by examining the production of viral proteins. This was done by plating 293 cells in 35-mm diameter plates at a density of 0.2×10$^6$ cells/plate. Following a 24 hour incubation, the culture medium was changed to IMEM supplemented with 2% FCS, and cells were infected for 2 hours at 37° C. with Ad-CFTR, or with Ad-CFTR which had been irradiated for various lengths of time. Newly synthesized proteins were labeled with [$^{35}$S]methionine (10 μCi/ml; specific activity, >1,000 μCi/mmol; Amersham) for 12 hours in methionine-free IMEM supplemented with 2% dialyzed FCS and 1% non-dialyzed FCS. Following incubation, the cells were washed twice with IMEM and twice with PBS, and were then centrifuged at 15,000×g for 5 minutes. The cell lysates were prepared by three cycles of freezing and thawing and analyzed on SDS-acrylamide gels as described above. The gels were dried and evaluated by autoradiography to visualize the $^{35}$S-labeled proteins. The presence of a 108 kilodalton (kDa) protein corresponding to newly synthesized Ad5 hexon protein evidenced the functionality of Ad-CFTR. Since preliminary studies confirmed that 120 seconds of UV exposure rendered Ad-CFTR incapable of directing synthesis of hexon protein in 293 cells, a range of UV doses corresponding to UV irradiation for 0 to 300 seconds were employed in these studies.

In parallel experiments, UV-irradiated Ad-CFTR was exposed to COS-7 cells in the presence of plasmid pRSVL, and luciferase activity was determined following a 48 hour incubation.

Figure 10B:
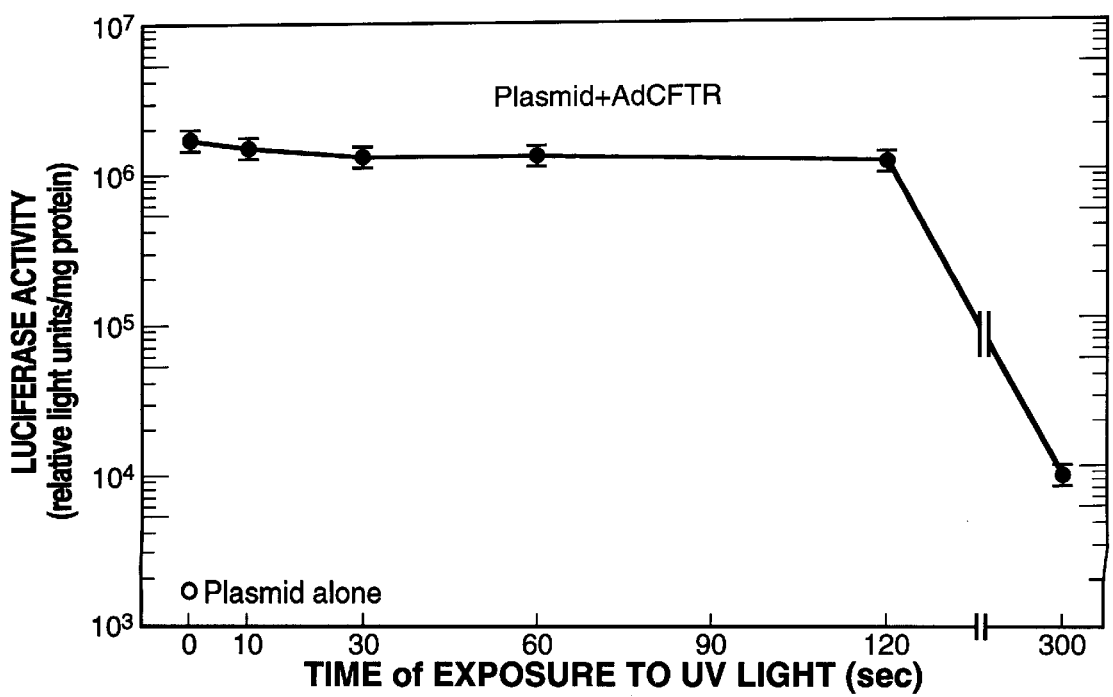
FIGS. 10A–10B illustrate the effect of UV radiation on adenoviral-mediated cointernalization of pRSVL: (A) autoradiogram of $^{35}$S-labeled proteins from 293 cells infected with Ad-CFTR that had been UV-irradiated for the lengths of time indicated; (B) graph of length of UV-irradiation of Ad-CFTR (sec) versus luciferase activity (RLU/mg cell lysate protein) for COS-7 cells incubated with pRSVL alone ($\circ$) or prior to infection with UV-irradiated Ad-CFTR ($\bullet$).
Figure 10A:
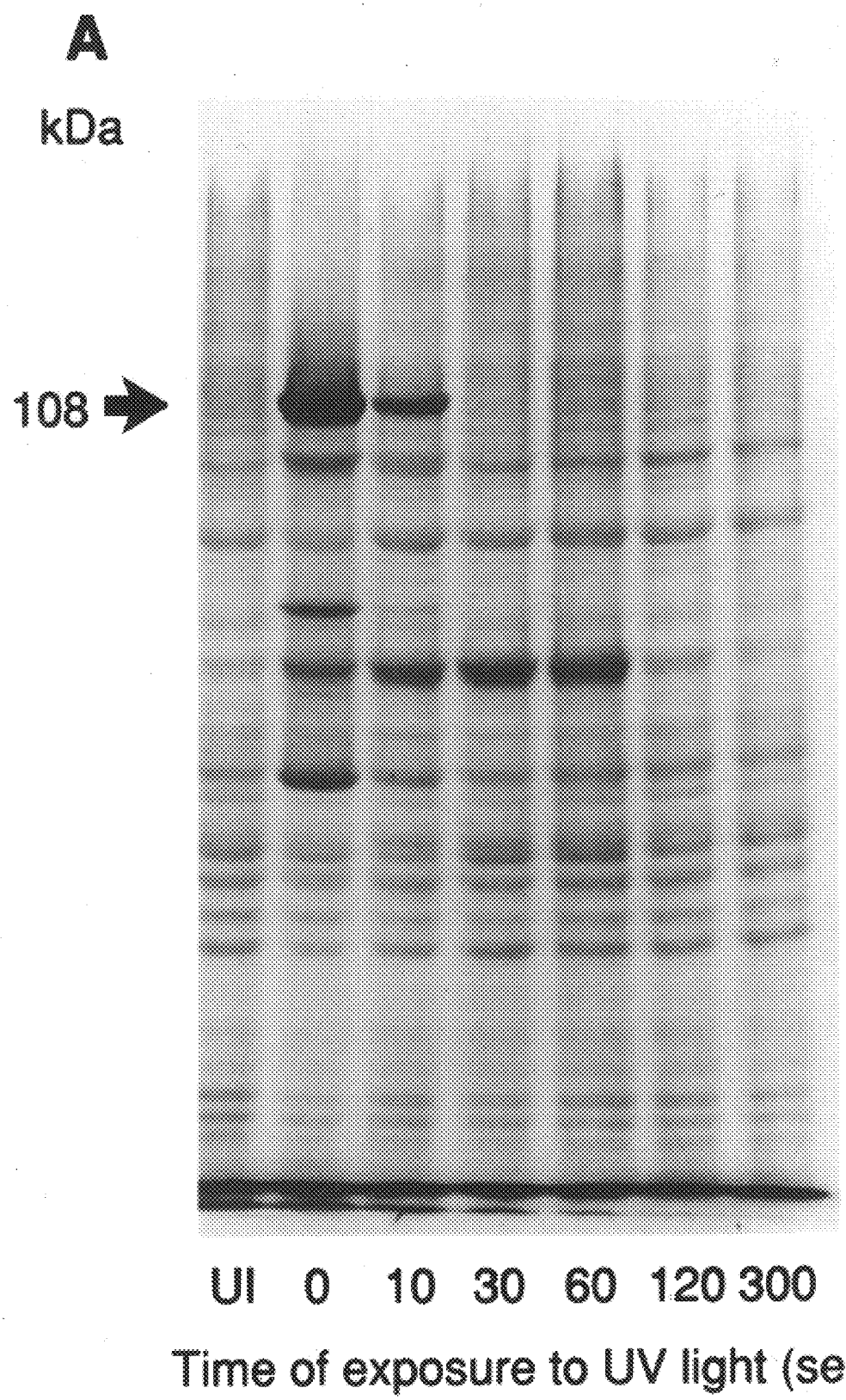

As presented in FIG. 10A, UV exposure of Ad-CFTR for 10 seconds impeded viral production of hexon protein by 50 to 60%. UV exposure for greater than 30 seconds resulted in complete loss of the ability of Ad-CFTR to produce viral proteins.

In contrast, UV exposure for up to 120 seconds resulted in only a slight inhibitory effect (i.e., less than a 20% reduction) on the ability of the virus to enhance transfer and expression of plasmid in COS-7 cells, as presented in FIG. 10B. However, UV-irradiation of Ad-CFTR for longer periods of up to 5 minutes resulted in the loss of the Ad-CFTR-mediated increase in luciferase activity, which was likely due to damage to the capsid proteins, and the subsequent inability of the capsid to bind target cells and undergo RME. UV-irradiation of Ad-CFTR for up to 60 seconds resulted in the increased expression of another protein of 56 kDa. However, with longer UV exposures, the expression of this protein was diminished. Since the 56 kDa protein is not found in assembled Ad-CFTR virions (data not shown), it is probably a virus-induced host protein.

These results confirm that the adenovirus vector-dependent enhanced expression of plasmid DNA does not require the functional viral genome, which is to be expected with respect to an RME-mediated process. Thus, even when the adenoviral genome has been destroyed by UV irradiation, the ability of the adenoviral vector to enhance DNA delivery remains intact.

EXAMPLE 10
Adenoviral-Mediated Augmentation of Cell Transfection with pRSVL is Dependent on the Adenoviral Capsid In this Example, the necessity of the adenoviral capsid for observation of the Ad-CFTR-mediated increase in transfer and expression of plasmid pRSVL in host cells was evaluated.

To investigate whether adenovirus particles devoid of any genome were able to enhance the delivery of plasmid DNA into cells, the effects of empty Ad-CFTR capsids were evaluated. Empty capsids of Ad-CFTR were extracted from the uppermost band (i.e., the lower-density band) present in the first CsCl (Boehringer-Mannheim, Indianapolis, Ind.) gradient employed in purification of Ad-CFTR (Rosenfeld et al., Cell, 68, 143–155 (1992)). This material was subjected to a second CsCl gradient, dialyzed against 50% glycerol containing 10 mM Tris (pH 7.4) and 1 mM MgCl$_2$, and kept frozen at –70° C.

To ensure that empty capsids were devoid of Ad-CFTR DNA, the properties of the empty capsids were compared with those of intact Ad-CFTR. The density of the empty capsids was determined by collecting the band from the second gradient and weighing 1 ml of this solution. The density of the empty capsids was found to be 1.23, as compared with a density of at least 1.34 for Ad-CFTR. The presence of proteins and DNA in the empty capsids as compared with in intact Ad-CFTR was determined by: (1) monitoring the absorbance at optical densities of 260 and 280 nm (i.e., OD$_{260}$ and OD$_{280}$) and determining protein concentration by the method of Bradford; (2) treating 100 μg of intact Ad-CFTR or empty capsids with SDS (final concentration, 1%) and proteinase K (final concentration, 50 μg/ml) for 18 hours, electrophoresing the sample on an agarose gel in the presence of ethidium bromide (i.e., to allow visualization of any DNA bands present), subjecting the sample to irradiation, depurination, denaturation and then neutralization prior to transfer, transferring the sample from the gel to a nylon membrane (Nytran; Schleicher & Schuell, Keen, N. H.), hybridizing the membrane with a $^{32}$p-labeled probe derived from the whole Ad-CFTR genome, and analyzing autoradiograms, as previously described (Rosenfeld et al., Cell, 68, 143–155 (1992)); and (3) electrophoresing the samples on a SDS-gel, staining, destaining and photographing the gel, and comparing protein patterns for empty capsids to those obtained for Ad-CFTR.

The OD$_{260}$/$_{280}$ absorbance ratios were 1.25 for Ad-CFTR, and 1.02 for empty capsids, as measured in aliquots with identical amounts of protein. While the concentration of DNA present in Ad-CFTR was 833 μg/ml, DNA was not detectable in empty capsids either by ethidium bromide staining of samples electrophoresed on agarose gels, or by Southern hybridization with a $^{32}$P-labeled Ad-CFTR DNA probe of electrophoresed samples transferred to a nylon membrane. These results indicate that the empty capsids were devoid of any substantial amount of DNA. However, analysis of the empty capsids by SDS-gel electrophoresis indicated that they appeared to contain fiber and the other viral proteins in stoichiometric amounts similar to those present in intact Ad-CFTR (data not shown).

To examine the capacity of empty adenoviral capsids to mediate the increased expression of pRSVL, COS-7 cells were exposed to different concentrations of empty capsids of Ad-CFTR in the presence of 5 μg of plasmid pRSVL for 2 hours in Opti-MEM® I medium. The medium was then changed to a serum-containing medium, and 48 hours later, luciferase activities were determined.

Figure 11:
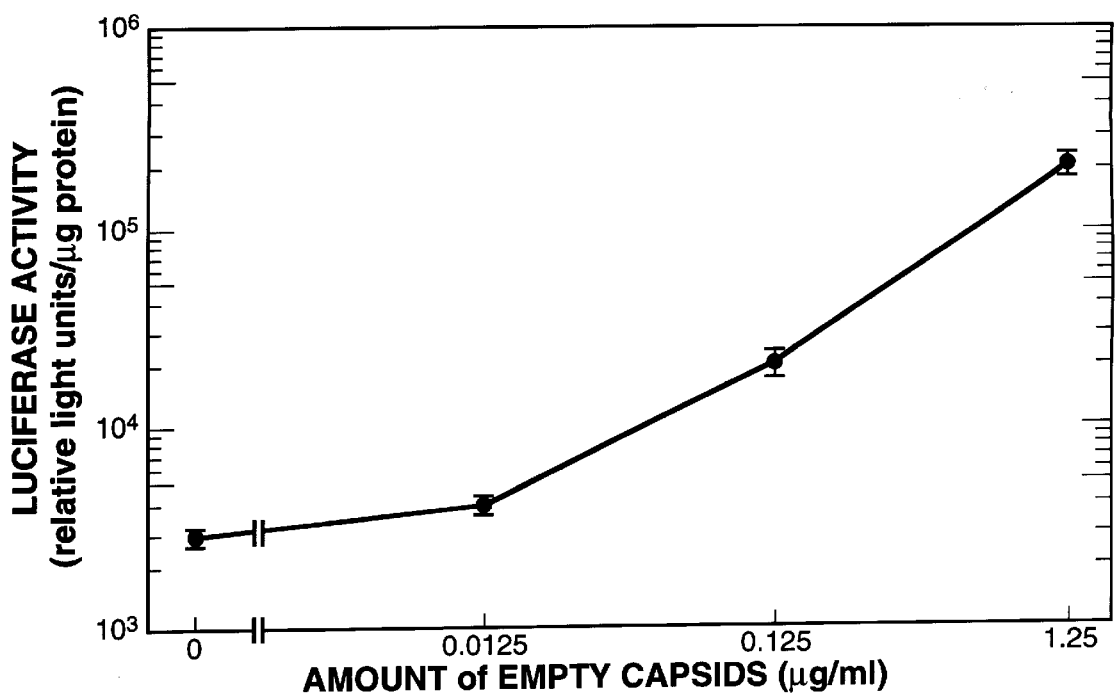
FIG. 11 is a graph of amount of empty capsids ($\mu$g/ml) versus luciferase activity (RLU/mg cell lysate protein) for COS-7 cells incubated with pRSVL and empty capsids of Ad-CFTR.

As presented in FIG. 11, empty capsids increased the expression of plasmid pRSVL in COS-7 cells in accordance with the amount of empty capsids added. The effectiveness of the empty capsids, however, appeared to be about 5 to 10 times less effective than Ad-CFTR in commanding RME of pRSVL.

These results validate that empty capsids are capable of mediating plasmid DNA delivery to host cells. In this respect, empty adenoviral capsids are less effective than intact adenoviral capsids. Since empty capsids possess the same stoichiometric amounts of fiber as does Ad-CFTR, it is unlikely that empty capsids bind to the cell receptor at lower efficiency. Possible explanations of the lesser effectiveness of Ad-CFTR which remain to be investigated include that the empty capsids may not be internalized into target cells with the same efficiency as Ad-CFTR, or are less efficient in disrupting endosomes.

EXAMPLE 11
Comparison of the Effect on Adenoviral-Mediated Augmentation of Cell Transfection with Plasmid DNA of Preincubation with Different Types of Cationic Agents In this Example, the possibility of increasing the adenoviral-mediated augmentation of cell transfection was investigated by exploring the effect of preincubation of the plasmid with different types of cationic agents capable of binding larger quantities of plasmid DNA.

In this respect, the efficacy of the Lipofectin® Reagent employed in Example 4 was compared with the efficacy of liposomes comprised of 1,2-bis(oleoyloxy)-3-(trimethylammonio)propane (DOTAP; Boehringer-Mannheim), a 1.5:1 molar ratio of the polycationic lipid 2,3-dioleyloxy-N-[2(sperminecarboxamido)ethyl]-N,N-dimethyl-1propanaminium trifluoroacetate (DOSPA) and the neutral lipid dioleoylphosphatidyl ethanolamine (DOPE) (LipofectAMINE™, Life Technologies Inc., Gaithersberg, Md.) as well as the efficacy of cationic agents such as the polycarbene, polybrene (or 1,5-dimethyl-1,5-diazaundecamethylene polymethobromide; Sigma). Notably, LipofectAMINE™ as well as Transfectam® Reagent (or dioctadecylamidoglycylspermine, or DOGS; Promega Corp., Madison, Wis.) were investigated as these liposomes contain additional head groups of the polyamine, spermine, which binds the inner groove of DNA. These reagents are considered polycationic liposomes as compared with the monocationic liposomes, Lipofectin® Reagent and DOTAP. All purchased liposomal reagents were used according to the instructions of the manufacturer.

Viruses and plasmids employed in this Example are as described in Example 1. However, the additional plasmid pCMVβgal was also employed (MacGregor et al., *Nucleic Acid Res.*, 17, 2365 (1989)). This vector contains the cytomegalovirus promotor driving expression of β-galactosidase as a reporter gene.

To study the expression of pCMVβgal plasmid in the presence of Ad-CFTR and the cationic agents, the experiments were done essentially as described in Example 1. Namely, $0.5 \times 10^6$ cells were seeded in 60-mm diameter plates. Twenty-four hours later, cells were washed with OPTI-MEM® I and incubated in the same medium for 2 hours. pCMVβgal (5 μg/plate) was preincubated with either Lipofectin® Reagent (20 μg), DOTAP (20 μg), polybrene (2 μg), Transfectam® Reagent (20 μg) or LipofectAMINE™ (20 μg), or in the absence of any cationic agents, for 30 minutes at room temperature, and the resultant solution was then added to the cell cultures. For some of the cultures, Ad-CFTR was also added (10 PFU/cell) along with the DNA solution. After 2 hours of incubation, the medium was changed to IMEM containing 10% FCS, and the cultures were incubated for an additional 20 hours. The cells were then scraped, washed twice with PBS, and evaluated for β-galactosidase activity.

β-galactosidase activity was detected in cell lysates essentially by a previously described protocol with some modifications. Pelleted cells were suspended in a buffer containing 30 mM sodium phosphate, pH 7.5, and were then lysed by three cycles of freezing and thawing. The samples were centrifuged at 15,000×g for 5 minutes, and were directly assayed for β-galactosidase activity. Portions of the cell lysates were incubated in separate wells of a 96-well plate (Becton Dickinson, Lincoln Park, N.J.) with 10.62 μM o-nitrophenyl β-D-galactopyranoside (ONPG; Sigma) in a final volume of 20 μl per well. Five-fold serial dilutions of up to 15625-fold were prepared for the enzyme assays, prior to addition of ONPG. After appropriate incubation of the reaction mixtures at 37° C., the absorbance was measured at 405 nm using an ELISA reader (Biorad, Richmond, Calif.). An absorbance reading of 1.0 was considered equivalent to 1.0 unit of β-galactosidase activity. β-galactosidase activity was expressed as units/mg protein present in the cell lysate.

Figure 12:
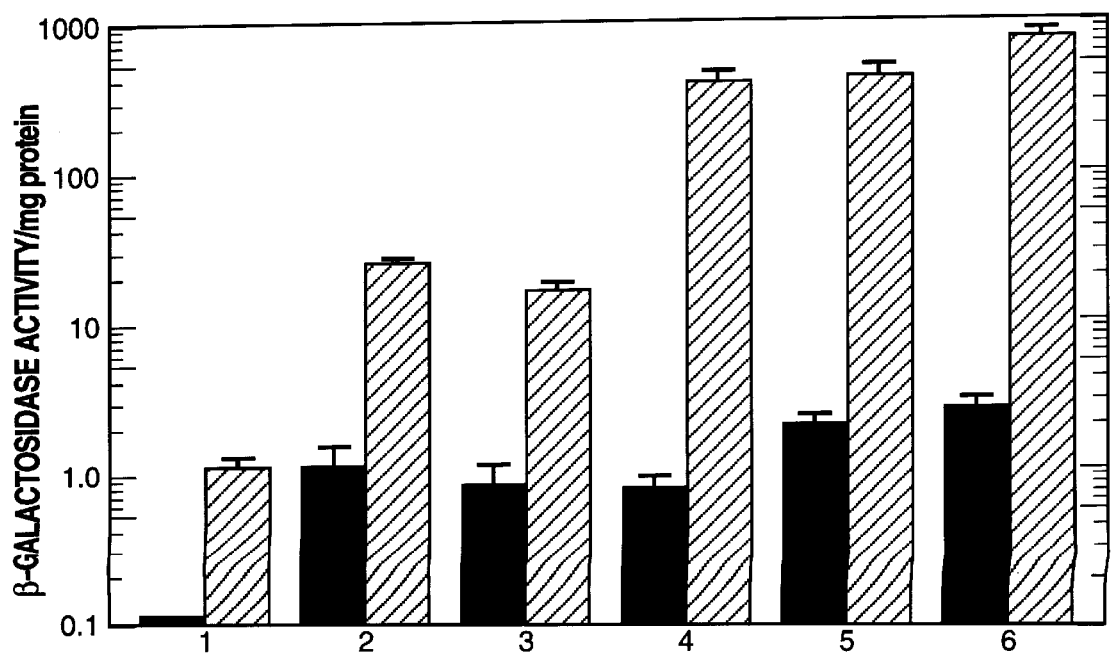
FIG. 12 is a bar chart showing $\beta$-galactosidase activity (units/mg cell lysate protein) for COS-7 cells incubated with pCMV$\beta$gal alone (panel 1) or along with Lipofectin® Reagent (panel 2), DOTAP (panel 3), polybrene (panel 4), Transfectam® Reagent (panel 5) and LipofectAMINE™ (panel 6) in the absence (solid bars) and presence (hatched bars) of Ad-CFTR.

As presented in FIG. 12, in COS-7 cells exposed to pCMVβgal alone, the enzyme activity was about 0.11 unit/mg protein. The activities obtained for COS-7 cells exposed to pCMVβgal plus either Ad-CFTR, Lipofectin® Reagent, DOTAP, polybrene, Transfectam® Reagent and LipofectAMINE™ were not substantially higher, and corresponded to 1.1, 1.1, 0.8, 0.75, 2.0, and 2.6 units/mg protein, respectively (i.e., FIG. 12, solid bars). These results corresponded to a 7–25 fold increase over the enzyme activity obtained when any of these reagents was employed in the absence of pCMVβgal.

To test for possible synergism between Ad-CFTR and the various cationic agents in augmentation of the expression of pCMVβgal, in a set of parallel experiments, COS-7 cells were exposed to pCMVβgal preincubated with the cationic agents in conjunction with exposure to Ad-CFTR. As presented in FIG. 12 (i.e., the hatched bars), in the presence of Ad-CFTR and either Lipofectins Reagent, DOTAP, polybrene, Transfectam® Reagent, or LipofectAMINE™, the enzyme activity obtained corresponded to 24, 16, 377, 419 and 742 units/mg protein, respectively. These results confirm a much higher increase in plasmid expression (i.e., a 145–6745 fold increase over the enzyme activity obtained when any of these reagents was employed in the absence of pCMVβgal) when Ad-CFTR infection was used along with incubation with cationic agents and pCMVβgal, as compared to incubation with pCMVβgal alone. Furthermore, the various reagents appear capable of augmenting Ad-CFTR-dependent expression of pCMVβgal in the following order of increasing effectiveness: monocationic liposomes (i.e., DOTAP, Lipofectin® Reagent), polycarbenes (i.e., polybrene), and polycationic liposomes (Transfectam® Reagent and LipofectAMINE™).

To confirm this order of effectiveness, COS-7 cells were incubated with pCMVβgal (15 μg) and Ad-CFTR (100 PFU/cell) alone, or in combination with either Lipofectin® Reagent (20 μg), polybrene (2 μg) or Transfectam® Reagent (20 μg), as described above. Following transfection, the amount of β-galactosidase activity per cell was quantified by staining the cells with 5-bromo-4-chloro-3-indolyl-β-D-galactopyranoside (X-gal; Boehringer-Mannheim). This was done by fixing cells for 5 minutes at 5° C. in a PBS solution containing 2% formaldehyde and 0.2% glutaraldehyde. Cells were then stained for 4 hours at 37° C. in a solution containing 5 mM $K_4Fe(CN)_6$, 5 mM $K_3Fe(CN)_6$, 2 mM $MgCl_2$, and 200 μg/ml X-gal. Observation of blue coloration of cells under a phase contrast microscope confirmed the presence of β-galactosidase within the cell. Either a random sampling of cells were counted (i.e., 100 cells in each of three different fields), or cells were photographed.

Figure 13A:
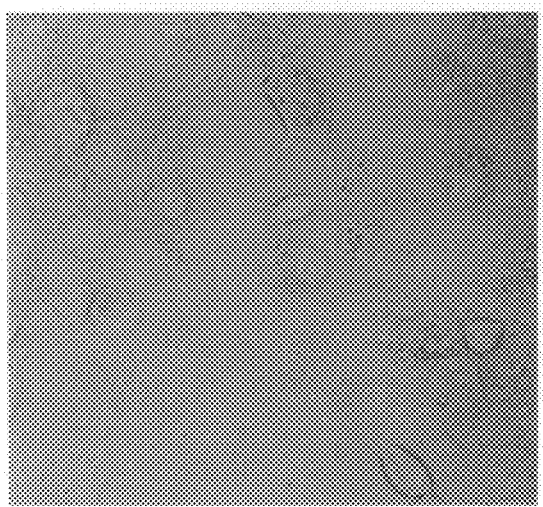
FIGS. 13A–13D are a series of phase contrast micrographs (1000×magnification) showing $\beta$-galactosidase activity in COS-7 cells transfected with pCMV$\beta$gal and Ad-CFTR alone (A) or in conjunction with Lipofectin® Reagent (B), polybrene (C), or Transfectam® Reagent (D).
Figure 13B:
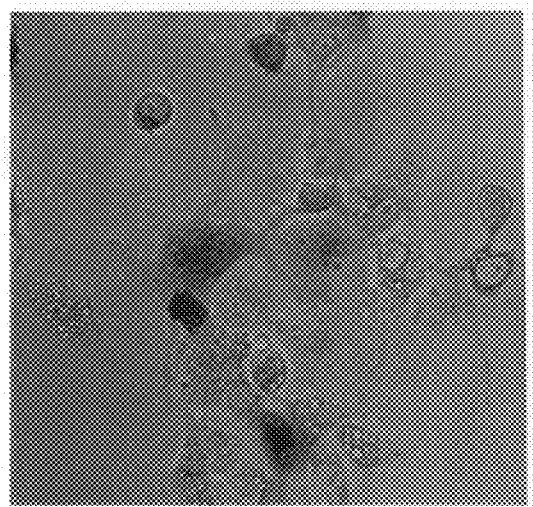
Figure 13C:
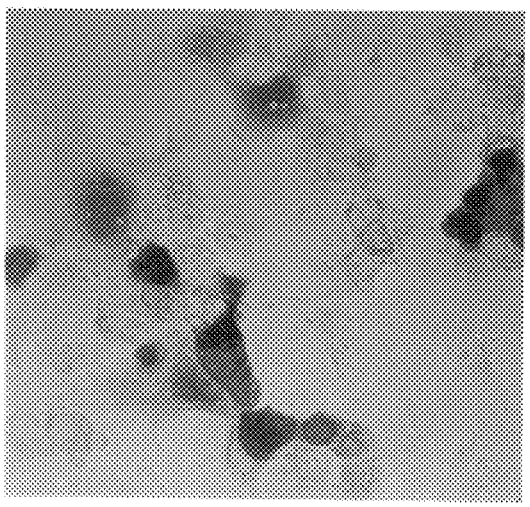
Figure 13D:
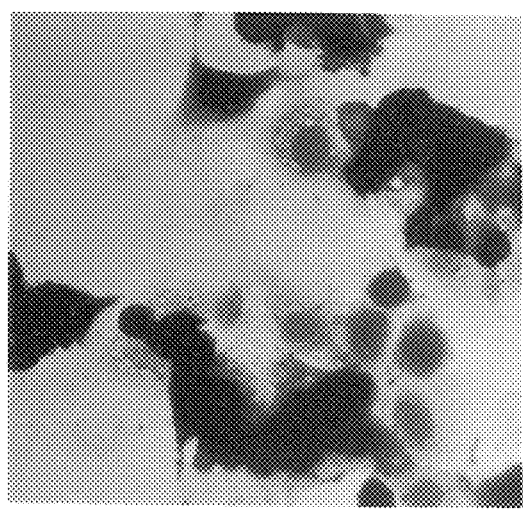

As presented in FIG. 13A, exposure of cells to both pCMVβgal and Ad-CFTR resulted in blue coloration of about 5 percent of the cells. Addition of Lipofectin® Reagent further increased the number of blue-appearing cells to about 10–20 percent, as indicated in FIG. 13B. Moreover, inclusion of polybrene (i.e., FIG. 13C) or Transfectam® Reagent (i.e., FIG. 13D) instead of Lipofectin® Reagent resulted in blue coloration of the majority of the cells.

These results are quantified in Table 4, column 1, and confirm that the various cationic agents tested are capable of augmenting Ad-CFTR-dependent expression of pCMVβgal in COS-7 cells in the following order of increasing effectiveness: monocationic liposomes, polycarbenes, and polycationic liposomes.

TABLE 4

Effect in Various Cell Types of Lipofectin ® Reagent, Polybrene, Transfectam ® Reagent and LipofectAMINE ™ on the Ad-CFTR-Mediated Increase in the Transfer and Expression of a Plasmid Containing a β-Galactosidase Reporter Gene.

| Treatment | Cos-7 | IB3-1 | RD | A204 | $C_2C_{12}$ |
|---|---|---|---|---|---|
| DNA | 0.33 ± 0.33 | 0 | 0 | 1.66 ± 0.33 | 0.33 ± 0.33 |
| DNA + Ad-CFTR | 7.0 ± 1.52 | 2.6 ± 0.33 | 0.66 ± 0.33 | 3 ± 0.5 | 3.66 ± 0.33 |
| DNA + Lipofectin ® Reagent | 3.33 ± 0.88 | 1.6 ± 0.66 | 1.66 ± 0.33 | 8.3 ± 1.45 | 1.66 ± 0.33 |
| DNA + Polybrene | 0.66 ± 0.33 | 0.33 ± 0.33 | 0.33 ± 0.33 | 6 ± 1.15 | 1.33 ± 0.33 |
| DNA + Transfectam ® Reagent | 21.3 ± 1.45 | 20 ± 1.2 | 9 ± 1.15 | 15.6 ± 2.33 | 7 ± 0.57 |
| DNA + LipofectAMINE ™ | 28 ± 1.5 | 27 ± 1.45 | 11 ± 1.78 | 22.6 ± 3.38 | 11 ± 1.15 |
| DNA + Lipofectin ® Reagent + Ad-CFTR | 21 ± 4.1 | 34 ± 2.5 | 2.25 ± 0.55 | 17 ± 1.1 | 6 ± 1.15 |
| DNA + Polybrene + Ad-CFTR | 94 ± 1.7 | 80 ± 1.2 | 70.6 ± 5.3 | 73 ± 5.2 | 71.6 ± 1.2 |
| DNA + Transfectam ® Reagent + Ad-CFTR | 98 ± 0.57 | 85 ± 2.33 | 81 ± 3.05 | 74 ± 2.4 | 77 ± 3.06 |
| DNA + LipofectAMINE ™ + Ad-CFTR | 99 ± 0.33 | 89.6 ± 2.08 | 90 ± 2.08 | 85 ± 1.32 | 82.6 ± 1.85 |

EXAMPLE 12
Confirmation of the Effectiveness of Different Cationic Agents in Enhancing Adenoviral-Mediated Augmentation of Cell Transfection with Plasmid DNA in Different Cell Lines In this Example, the ability of the various cationic agents to increase adenoviral-dependant plasmid transfer in different cell lines was examined and compared.

Additional cell cultures employed in this Example include RD, a human embryonal rhabdomyosarcoma cell line (ATCC CCL 136), A204, a human rhabdomyosarcoma cell line (ATCC HTB 82), and $C_2C_{12}$, a mouse muscle myoblast cell line (ATCC CRL 1773). These cultures were grown as monolayers in IMEM supplemented with 10% FCS, 50 units/ml penicillin and 50 μg/ml streptomycin (all from Biofluids). Furthermore, IB3-1 (obtained from G. Cutting, Johns Hopkins University, Baltimore, Md.) was also employed. This cystic fibrosis respiratory epithelial cell line was originally derived from the bronchial epithelium of an individual with CF (i.e., a compound heterozygote with the common ΔF508 CF mutation and the W1282X mutation), and was cultured on collagen- (Vitrogen; Collagen Corporation, Palo Alto, Calif.) and fibronectin- (CalBiochem, San Diego, Calif.) coated plates in LHC-8 serum-free medium (Biofluids) supplemented with 15 μg/ml endothelial cell growth supplement (Becton Dickinson, Oxnard, Calif.), 50 units/ml penicillin and 50 μg/ml streptomycin (all from Biofluids). For transfections, IB3-1 cells were routinely grown on fibronectin- (Pronactin, Biosource International, San Diego, Calif.) coated coverglass chambers (Nunc, Inc., Roskilde, Denmark).

For these expaeriments, COS-7 cells, IB3-1 cells, RD cells, A204 cells, and $C_2C_{12}$ cells were exposed to pCMVβgal (5 μg) in the presence of either Lipofectin® Reagent (20 μg), polybrene (2 μg), Transfectam™ Reagent (20 μg) or LipofectAMINE™ (20 μg) both in the absence and presence of Ad-CFTR (10 PFU/cell), and following β-galactosidase staining, the number of cells appearing blue was scored by counting 100 cells in 3 separate fields. The experiments were performed in triplicate, and the average and standard error of the mean were determined.

As presented in Table 4, in each of the cell lines tested, less than 2% of the cells stained positive for β-galactosidase following exposure to pCMVβgal alone, and less than 30% of cells showed detectable blue color when any one of the cationic agents was added individually along with pCMVβgal. However, when Lipofectin® Reagent treatment was accompanied by Ad-CFTR infection, the percentage of blue cells obtained varied from 2.25 (i.e., observed for RD cells) to 20 (i.e., observed for COS-7 cells). When Ad-CFTR infection accompanied preincubation of pCMVβgal with either polybrene, Transfectam™ Reagent or LipofectAMINE™, the percentage of blue cells obtained varied from 94–99% observed for COS-7 cells, 80–90% observed for IB3-1 cells and 70–90% observed for muscle cells (i.e., RD, A204 and $C_2C_{12}$ cells). For each cell line, the combination of Ad-CFTR infection and plasmid preincubation with LipofectAMINE™ was found to result in the highest level of β-galactosidase staining. Moreover, the results also confirm that Ad-CFTR infection used in combination with polybrene or preincubation with a polycationic liposome resulted in significantly better transfection than when Ad-CFTR infection was employed in combination with preincubation with a monocationic liposome, such as Lipofectin® Reagent.

Accordingly, the results validate that the present transfection protocol in which adenovirus infection is used in conjunction with DNA preincubation with liposomes can be employed for a variety of cell types. Although monocationic liposomes such as Lipofectin® Reagent were able to augment Ad-CFTR-mediated transfection, polycationic liposomes were about 3–40 times better than monocationic liposomes in this respect. Moreover, certain polycationic liposomes used in conjunction with adenoviral infection were able to effect transfection in about 90 percent of the cells examined, thus attesting to the efficiency of this method of nucleic acid transfer.

EXAMPLE 13
Effect of Polycationic Liposome Composition on the Ad-CFTR-Mediated Increase in the Expression of the pCMVβgal Plasmid In this Example, the possibility of increasing the adenoviral-mediated transfection-enhancing ability of the polycationic liposome LipofectAMINE™ by altering the lipid composition the liposomes was explored. Namely, since LipofectAMINE™ is comprised of a 1.5:1 DOSPA:DOPE molar ratio, the effect of varying the ratio of DOSPA to DOPE on the Ad-CFTR-mediated increase in the expression of pCMVβgal in transfected cells was investigated.

For these experiments, polycationic LipofectAMINE™-related liposomes comprised of DOSPA:DOPE molar ratios of 1.5:1, 1:1, 0.5:1, 0.25:1, 0.1:1 were constructed. Liposomes containing the various molar ratios of DOSPA to DOPE were formulated by drying lipids under argon and then placing the samples under vacuum for 5 hours. The lipids were resuspended in distilled water, and were sonicated under argon using a horn bath sonicator for 30 minutes at 12° C. Transfections with pCMVβgal (5 μg) using the newly synthesized polycationic liposomes either alone or with Ad-CFTR (10 PFU/cell) were conducted in IB3-1 cells. Resultant β-galactosidase activities were determined, and the average and standard error of the mean were calculated based on triplicate determinations.

Figure 14:
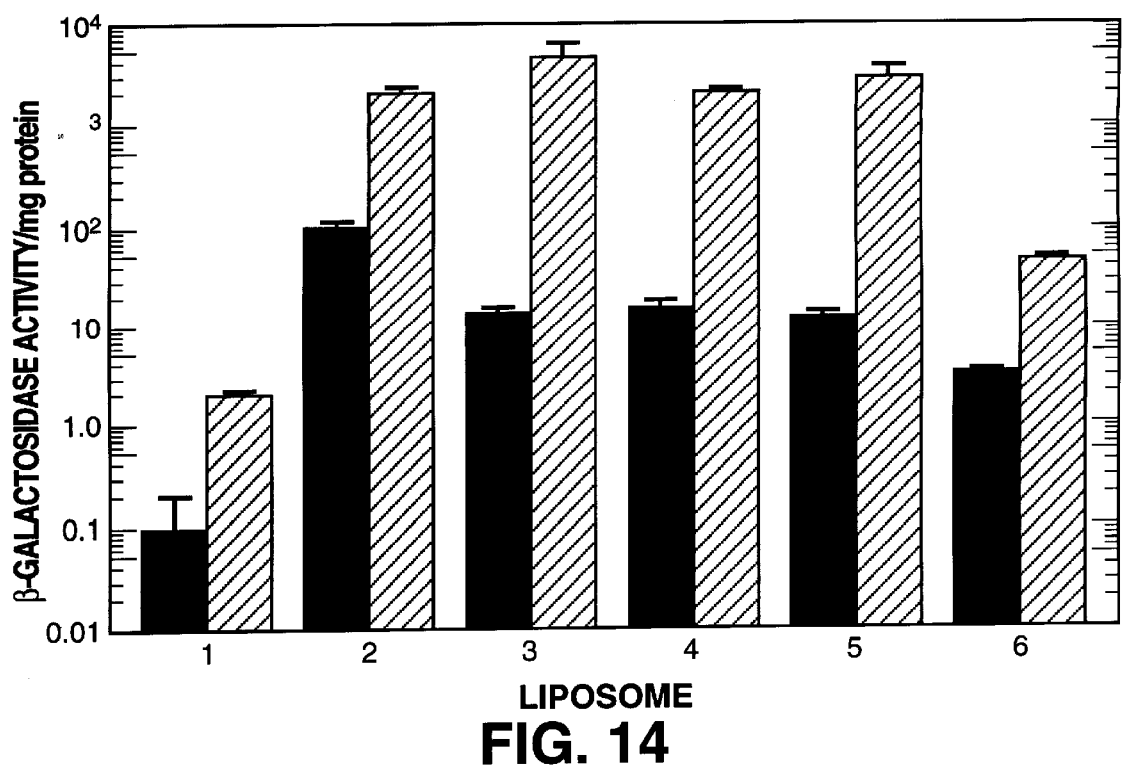
FIG. 14 is a bar chart showing $\beta$-galactosidase activity (units/mg cell lysate protein) for IB3-1 cells incubated with pCMV$\beta$gal alone (panel 1) or with liposomes composed of the DOSPA:DOPE molar ratios corresponding to 1.5:1 (panel 2), 1:1 (panel 3), 0.5:1 (panel 4), 0.25:1 (panel 5), and 0.1:1 (panel 6) in the absence (solid bars) and presence (hatched bars) of Ad-CFTR.

As demonstrated in FIG. 14, in the absence of Ad-CFTR (solid bars), a maximum β-galactosidase activity corresponding to about 109 units/mg protein was obtained using polycationic liposomes comprised of a DOSPA:DOPE molar ratio of 1.5:1 (i.e., using LipofectAMINE™). The β-galactosidase activity decreased in accordance with the decrease in the DOSPA:DOPE molar ratio, down to a level of 3.2 units/mg protein in the presence of liposomes comprised of a DOSPA:DOPE molar ratio of 0.1:1.

In comparison, pCMVβgal transfection in the presence of both Ad-CFTR and the polycationic liposomes (hatched bars) yielded the highest β-activity of 4689 units/mg protein obtained for liposomes comprised of a DOSPA:DOPE molar ratio of 1:1. This enzyme activity was at least two times higher than the activity obtained using liposomes comprised of DOSPA:DOPE molar ratios of either 1.5:1 or 0.5:1, which only yielded enzyme activities of 2027 and 2146 units/mg protein, respectively. Further, the maximal activity was 50–100 times higher than the enzyme activity obtained using Ad-CFTR in the presence of polycationic liposomes comprised of DOSPA:DOPE molar ratios of 0.25:1 or 0.1:0, which only yielded enzyme activities of 29 and 54 units/mg protein, respectively.

These results confirm that although the transfection efficiency of LipofectAMINE™ in the absence of Ad-CFTR is higher than the other polycationic liposomes tested, in the presence of Ad-CFTR, liposomes comprised of a DOSPA:DOPE molar ratio of 1:1 are superior to LipofectAMINE™ in augmenting adenoviral-mediated transfection.

EXAMPLE 14
Effect of Other Monocationic Liposomes on the Ad-CFTR-Mediated Increase in the Expression of the pCMVβgal Plasmid In this Example, the ability of various monocationic liposomes other than Lipofectin® Reagent to effect an increase in adenoviral-mediated transfection was explored.

The monocationic liposomes 143-8, 143-7, 75-7, 143-4 and LipofectACE™ (Gibco/BRL) were synthesized essentially as in Example 13 using, respectively, a 1:1 molar ratio of 1,2-dioleyl--3dimethylamino propyl-B-hydroxyethylammonium acetate (i.e., DORI ETHER) and DOPE, a 2:1 molar ratio of DORI ETHER and DOPE, a 1:1 molar ratio of N-[2-[(3-aminopropyl)amino]ethyl]-N,N-dimethyl-2,3-bis(octadecenyloty)-1-propaninium dibromide (i.e., DORI ETHER Propylamine) and DOPE, a 1:1 molar ratio of N-(2-bromoethyl)-N,N-dimethyl-2,3-bis(9-octadecenyloty)-1-propananinium bromide (i.e., DORI ETHER Bromo) and DOPE, and 1:2.5 (w/w) ratio of dimethyl dioctadecylammonium bromide (DDAB)and DOPE.

Figure 15:
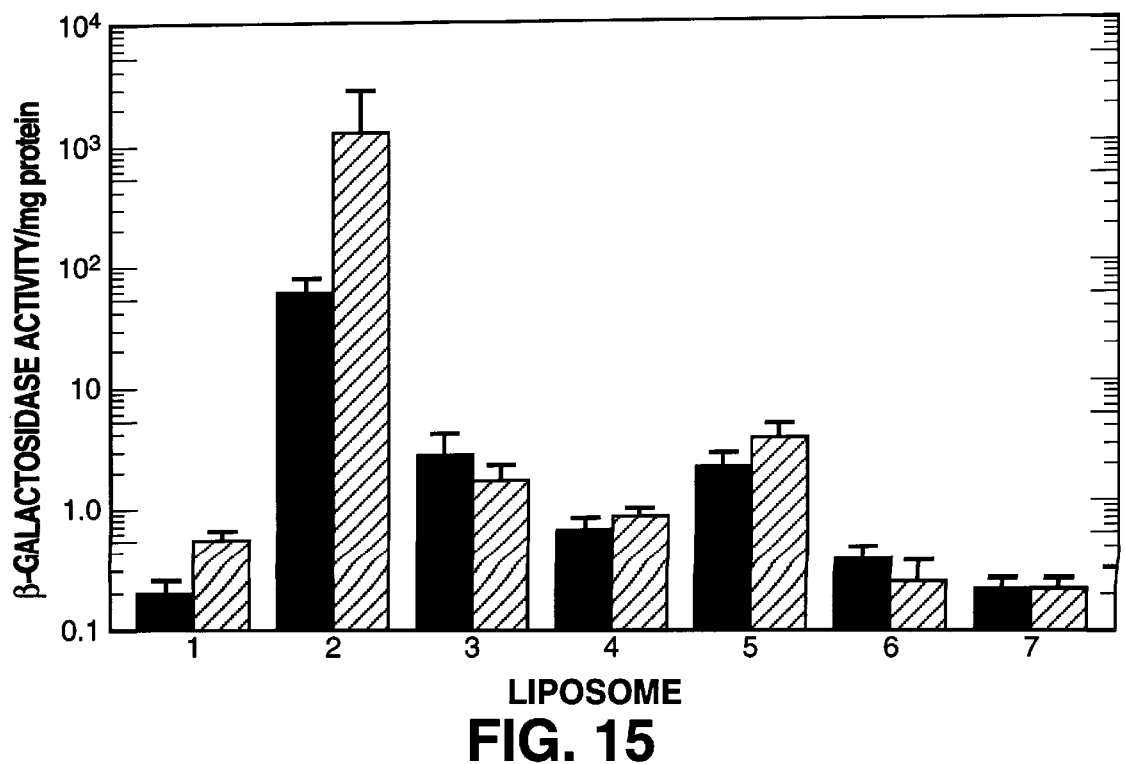
FIG. 15 is a bar chart showing $\beta$-galactosidase activity (units/mg cell lysate protein) for IB3-1 cells incubated with pCMV$\beta$gal alone (panel 1) or with the liposomes LipofectAMINE™ (panel 2), 143-8 (panel 3), 143-7 (panel 4), 143-4 (panel 5), 76-7 (panel 6), and LipofectACE™ (panel 7) in the absence (solid bars) and presence (hatched bars) of Ad-CFTR.

IB3-1 cells were exposed to pCMVβgal (5 μg) and either the polycationic liposome LipofectAMINE™, or the various synthesized monocationic liposomes in the absence and presence of infection with Ad-CFTR (10 PFU/cell), and β-galactosidase activities were subsequently determined. As presented in FIG. 15, of all the liposomes, LipofectAMINE™ effected the highest β-galactosidase levels in host cells used either in the absence (solid bars) or in the presence (hatched bars) of infection with Ad-CFTR. only the monocationic liposomes 143–7 and 143–4 were able to effect even a slight increase in β-galactosidase activity when incorporated into the transfection protocol.

These results confirm the superiority of polycationic liposomes as compared with monocationic liposomes in augmenting adenoviral-mediated cell transfection.

EXAMPLE 15
Effect of Liposome Vesicle Size on the Ad-CFTR-Mediated Increase in the Expression of the pCMVβgal Plasmid In this Example, the possibility of increasing the ability of the polycationic liposome LipofectAMINE™ to enhance adenoviral-mediated transfection by altering the vesicle size was explored.

Liposomes were prepared as in Example 13, and vesicles of different size were formed by resuspending lipids in distilled water, then passing the suspension through a polycarbonate filter with various pore sizes by means of a Liposofast apparatus (Avestin Inc., Ottawa, ON).

Figure 16:
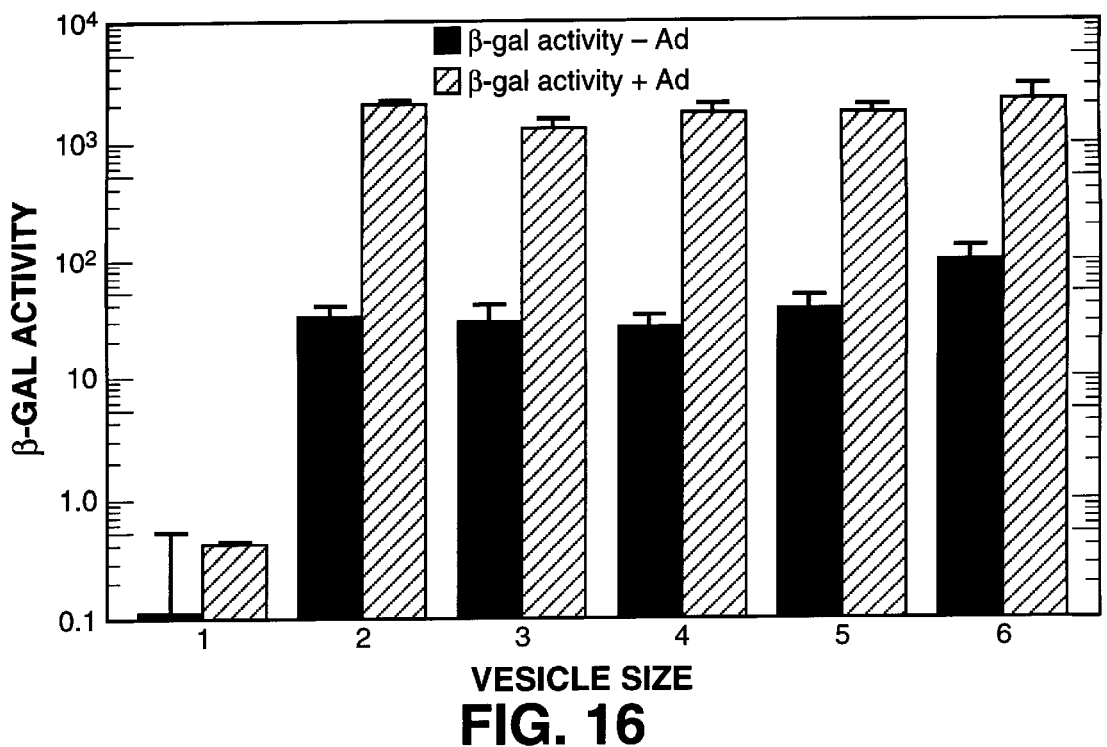
FIG. 16 is a bar chart showing $\beta$-galactosidase activity (units/mg cell lysate protein) for IB3-1 cells incubated with pCMV$\beta$gal alone (panel 1) or along with vesicles of 100 nm (panel 2), 200 nm (panel 3), 400 nm (panel 4), in size, or LipofectAMINE™(panel 5), or a mixture of the different size vesicles (panel 6) in the absence (solid bars) and presence (hatched bars) of Ad-CFTR.

LipofectAMINE™-type liposomes of vesicle sizes ranging from 100–400 nm were constructed and tested for their ability to enhance pCMVβgal expression in IB3-1 cells. Cells were exposed to pCMVβgal (5 μg) and the various polycationic liposomes in the absence or presence of Ad-CFTR (10 PFU/cell), and β-galactosidase activities were determined. As presented in FIG. 16, there was no substantial difference between the transfection efficiency of the different liposomes which corresponded to their differing sizes when employed either in the absence (solid bars) or in the presence (hatched bars) of infection with Ad-CFTR.

EXAMPLE 16
Liposome and Ad-CFTR-mediated Increase in the Expression of a Plasmid Containing the CFTR cDNA In this Example, the possibility of using the adenoviral-mediated transfection protocol described herein to evaluate expression of the PCMVCFTR plasmid which codes for the CFTR protein was evaluated.

The plasmid vector pCMVCFTR (Yoshimura et al., *Nucleic Acids Res.*, 20, 3233–40 (1992)) contains a full length human CFTR cDNA under the control of the cytomegalovirus promotor. Additionally employed in this Example was the vector Ad.RSVβgal. The Ad5-based vector Ad.RSVβgal contains the Rous sarcoma virus long terminal repeat as a promotor driving the expression of a β-galactosidase reporter gene, and also contains the SV40 nuclear localization signal to facilitate the detection of protein expression (Mastrangeli et al., *J. Clin. Invest.*, 91, 225–34 (1993)).

For these studies, polycationic liposomes comprised of a DOSPA:DOPE molar ratio of 1:1 were employed. IB3-1 cells were exposed to pCMVCFTR plasmid alone or in the absence and/or presence of Ad.RSVβgal or liposomes for 20 hours using the transfection protocol described in Example 4. The presence and functionality of the CFTR protein were investigated by monitoring cAMP-dependent Cl⁻ion efflux from IB3-1 cells. Ion efflux was monitored by incubating IB3-1 cells in cell culture medium containing 10 mM of the Cl⁻-sensitive fluorescent dye SPQ (6-methoxy-N-(3-sulfopropyl) quinolinium (Molecular Probes, Inc., Eugene, Oreg.) for another 18 hours. Unincorporated dye was then washed from the cells, and the cultures were incubated for 10 minutes in a buffer (pH 7.4) containing 135 mM NaI, 2.4 mM K$_2$HPO$_4$, 0.6 mM KH$_2$PO$_4$, 1 mM MgSO$_4$, 1 mM CaSO$_4$, 10 mM HEPES, and 10 mM glucose. The SPQ was excited at 350 nm, and fluorescent images were acquired for 3 minutes at 1 minute intervals. The buffer solution bathing the cells was then exchanged for buffer in which NaI was replaced with NaNO$_3$, and the fluorescence measurements were acquired for an additional 7 minutes. The changes accompanying an increase in Cl$^-$ permeability due to cAMP stimulation of the CFTR protein were measured by replacing the NaNO$_3$ buffer solution with a buffer solution containing 20 $\mu$M forskolin (Sigma), 200 $\mu$M cpt-cAMP (Sigma), and 500 $\mu$M -3-isobutyl-1-methylxanthine (IBMX) (Sigma). The fluorescence was monitored for an additional 10 minutes. Fluorescence images acquired at 450 nm from at least 20–30 cells/field were digitized, averaged for 8 frames, and quantified using a high-resolution CD camera (Videoscope International, Herdone, Va.) along with the Image1-Fluor software package (Universal Imaging, West Chester, Pa.). All fluorescent images were acquired at 37° C.

Figure 17A:
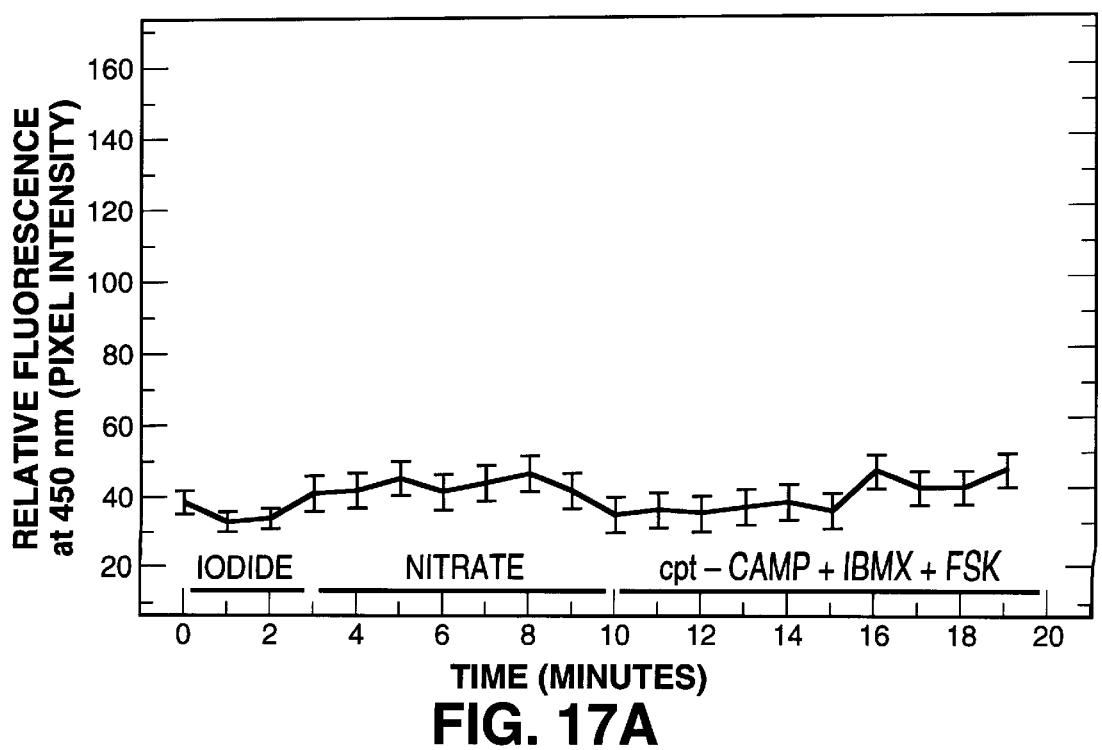
FIGS. 17A–17D is a series of graphs of time (minutes) versus relative fluorescence at 450 nm (in pixel intensities)
Figure 17B:
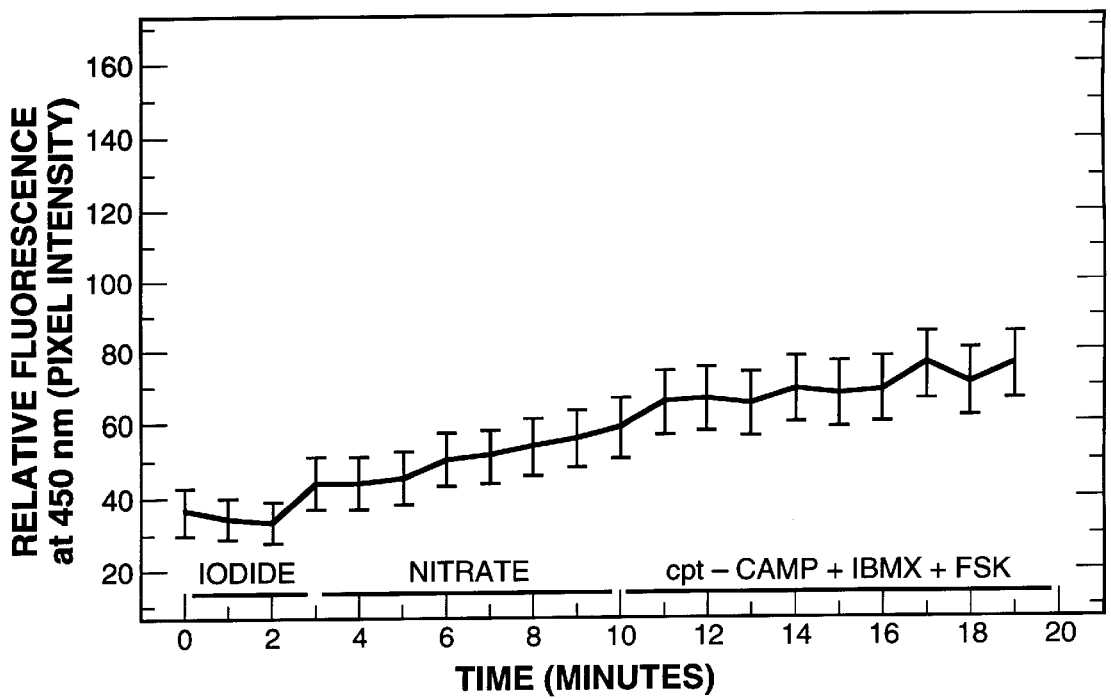
Figure 17C:
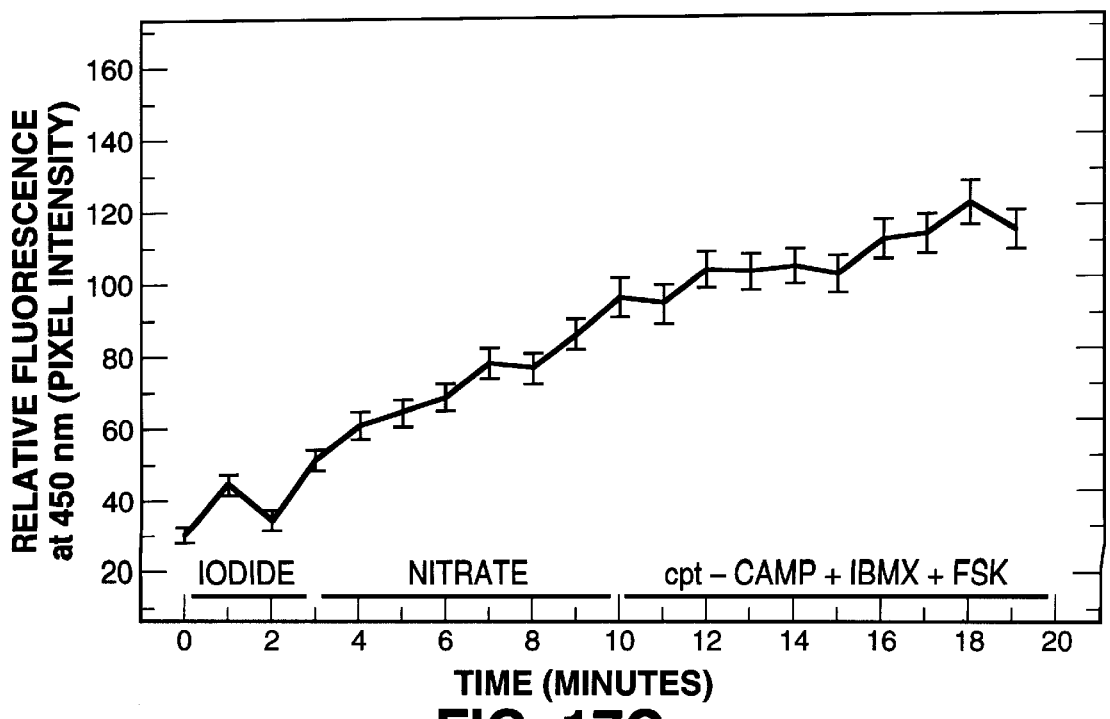
Figure 17D:
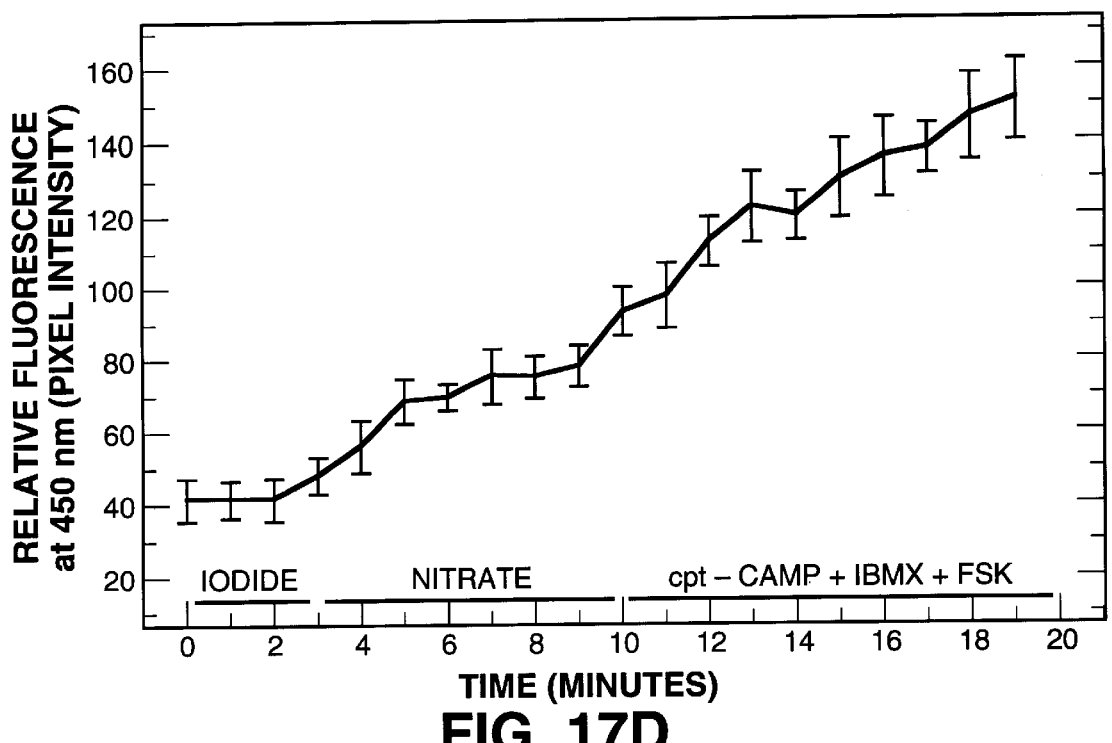

As presented in FIG. 17A, cells exposed to the PCMVCFTR plasmid alone demonstrated a fluorescence signal of about 40 pixels in intensity. Exposure of IB-3 cells to PCMVCFTR plus either Ad.RSVβgal (FIG. 17B) or polycationic liposomes (FIG. 17C) resulted in a fluorescence signal of at most about 75 and 120 pixels, respectively. The maximum fluorescence signal greater than 150 pixels in intensity was obtained when cells were exposed to all three components, i.e., the polycationic liposomes as well as the PCMVCFTR and Ad.RSVβgal plasmids, as presented in FIG. 17D.

These results confirm not only that Ad.RSVβgal can mediate transfection of IB3-1 cells with a CFTR cDNA-encoding plasmid, but also that such transfection can be augmented by preincubation of plasmid DNA with liposomes comprised of a 1:1 DOSPA:DOPE molar ratio. This successful transfer of a CFTR cDNA to cultured cells defective in CFTR protein supports the potential applicability of this approach to in vivo gene therapy in lung epithelial cells normally defective in CFTR protein.

EXAMPLE 17
Viability of Cells Following Transfection Mediated by Ad-CFTR and Augmented by Preincubation of Plasmid with Polycationic Liposomes In this Example, the effect on cell viability of the adenoviral-mediated transfection protocol described herein was evaluated.

In order to evaluate any effect on cell viability, IB3-1 cells were transfected with pCMVgal plasmid either alone or along with one or both of Ad-CFTR and liposomes comprised of a 1:1 DOSPA:DOPE molar ratio as described in Example 16. Following transfection, cells were removed from the tissue culture plates using trypsin, and were suspended in 1 ml of Hanks' Balanced Salt Solution (Mediatech, Herndon, Va.) supplemented with 1% FCS. 40 $\mu$l aliquots were then mixed with 40 $\mu$l of 1% trypan blue, and cells were visualized under a phase contrast microscope. In parallel, 0.8 ml of the cell suspension was treated with 50 $\mu$l of propidium iodide (20 $\mu$g/ml, Calbiochem, La Jolla, Calif.), and cells were visualized using a fluorescent microscope. Three fields of 100 cells each were counted, and cells which took up the blue or fluorescent dye were scored as non-viable.

For all of the conditions tested, i.e., transfection involving exposure of IB-3 cells to pCMVβgal plasmid alone, or combined with exposure to Ad-CFTR, polycationic liposomes, or polycationic liposomes plus Ad-CFTR, less than 10% of the cells examined in each case were non-viable following transfection (data not shown).

These results confirm the absence of substantial toxicity of adenoviral-mediated transfection, or of augmentation of such transfection by preincubation of plasmid with polycationic liposomes. Moreover, the results strongly support the applicability of this highly efficient method of transfection for in vivo nucleic acid transfer, as the DNA transfection protocol using Ad alone or in conjunction with polycationic molecules resulted in death of less 10% of cells examined in in vitro transfections.

EXAMPLE 18
In Vivo Use of the Method of Ad-Mediated Transfection Augmented by Cationic Agents In this Example, the method of adenoviral-mediated transfection and method of augmentation of such transfection with use of cationic agents as may be employed in vivo is described.

The present invention may be utilized in the treatment of diseases and disorders which may be associated with, or treatable by an alteration in the pattern of gene expression. Such diseases and conditions include but are not limited to IDs including diabetes, cystic fibrosis, multiple sclerosis and certain types of cancer. Similarly, the method of the present invention could be employed in the treatment of inflammatory disorders, viral infections and wasting disorders, such as those mediated by tumor necrosis factor. Moreover, the method could be employed to deliver pharmacologics such as antihypertensives and anticoagulants, or receptor agonists or antagonists.

To this end, nucleic acids including DNA, RNA or PNA can be delivered either in vitro or in vivo. The adenoviral-mediated method of transfection described herein can be employed in direct in vivo applications, such as, for instance, by administration of the various components of the invention via intratracheal instillation or aerosol administration. Alternatively, the method can be employed in vitro, wherein in vitro transfection of some of the cells of the host is performed, followed by the reintroduction of the cells into the host by a means such as injection. This method is advantageous since it allows the culture to be screened for transfectants prior to reintroduction into the host, and even potentially allows for enrichment of transfected cells using a selection protocol such as is known in the art (e.g., geneticin or G418 resistance as a consequence of transfer of a marker gene).

Of the IDs which may potentially be treated using the method of the present invention, cystic fibrosis is particularly relevant. CF is the most common, lethal inherited disorder in the Caucasian population (Hamosh et al. *J. Clin. Invest.*, 88, 1880–85 (1991)). The vector Ad-CFTR, employed in the method of the present invention may be particularly useful in this respect.

All of the references cited herein, including patents, patent applications, and publications, are hereby incorporated in their entireties by reference, as are the additional references by Seth et al., *J. Virol.*, 68, (1994) and Yoshimura et al., *J. Biolog. Chem.*, 268, 2300–2303 (1993).

While this invention has been described with an emphasis upon a preferred embodiment, it will be obvious to those of ordinary skill in the art that variations in the preferred composition and method may be used, including variations due to improvements in the art, and that it is intended that the invention be practiced otherwise than as specifically described herein, to encompass these variations. Accordingly, this invention includes all modifications encompassed within the spirit and scope of the invention as defined by the following claims.

What is claimed is:

1. A method of introducing a nucleic acid into a eukaryotic cell which can be infected by adenovirus which comprises contacting said cell with, in any order or simultaneously, said nucleic acid and an adenovirus so as to result in a cell with said nucleic acid therein, wherein said nucleic acid is not bound to any molecule which effects entry of said nucleic acid into said cell.

2. The method of claim 1, wherein said cell is contacted with said adenovirus less than about 8 hours after, or less than about 8 hours before, said cell is contacted with said nucleic acid.

3. The method of claim 1, wherein said cell is contacted with said adenovirus less than about 2 hours after, or less than about 2 hours before, said cell is contacted with said nucleic acid.

4. The method of claim 1, wherein said nucleic acid is DNA.

5. The method of claim 1, wherein said nucleic acid is RNA.

6. The method of claim 1, wherein said nucleic acid is PNA.

7. The method of claim 1, wherein said eukaryotic cell is in vivo.

8. The method of claim 1, wherein said eukaryotic cell is in vitro.

9. The method of claim 1, wherein said eukaryotic cell is selected from the group consisting of mammalian and avian cells.

10. The method of claim 9, wherein said eukaryotic cell is selected from the group consisting of ungulate, feline, and canine cells.

11. The method of claim 9, wherein said eukaryotic cell is a human cell.

12. The method of claim 1, wherein about 20 to about 2000 placque forming units of adenovirus are present per eukaryotic cell to be contacted.

13. The method of claim 1, wherein said adenovirus is a wild-type strain.

14. The method of claim 1, wherein said adenovirus comprises genetic material with at least one modification therein.

15. The method of claim 14, wherein said modification renders said adenovirus replication-deficient.

16. The method of claim 14, wherein said modification is selected from the group consisting of addition of a DNA segment, rearrangement of a DNA segment, deletion of a DNA segment, replacement of a DNA segment, methylation of unmethylated DNA, demethylation of methylated DNA, and introduction of a DNA lesion.

17. The method of claim 14, wherein said modification alters the cell binding, endosomal lysis, or intracellular targeting capabilities of the adenovirus.

18. The method of claim 1, wherein said adenovirus comprises empty capsids.

19. The method of claim 1, wherein said adenovirus has been inactivated.

20. A method of introducing a nucleic acid into a eukaryotic cell which can be infected by adenovirus which comprises contacting said cell with, in any order or simultaneously, said nucleic acid, an adenovirus, and a cationic agent which interacts with cell surfaces or nucleic acids so as to result in a cell with said nucleic acid therein, wherein said nucleic acid is not bound to any molecule which effects entry of said nucleic acid into said cell other than, optionally, said cationic agent.

21. The method of claim 20, wherein said nucleic acid and said cationic agent are mixed together and incubated prior to contacting said cell.

22. The method of claim 21, wherein said cell is contacted with said adenovirus less than about 8 hours after, or less than about 8 hours before, said cell is contacted with said incubated nucleic acid and cationic agent.

23. The method of claim 21, wherein said cell is contacted with said adenovirus less than about 2 hours after, or less than about 2 hours before, said cell is contacted with said incubated nucleic acid and cationic agent.

24. The method of claim 20, wherein said nucleic acid is DNA.

25. The method of claim 20, wherein said nucleic acid is RNA.

26. The method of claim 20, wherein said nucleic acid is PNA.

27. The method of claim 20, wherein said eukaryotic cell is in vivo.

28. The method of claim 20, wherein said eukaryotic cell is in vitro.

29. The method of claim 20, wherein said eukaryotic cell is selected from the group consisting of mammalian and avian cells.

30. The method of claim 29, wherein said eukaryotic cell is selected from the group consisting of ungulate, feline, and canine cells.

31. The method of claim 29, wherein said eukaryotic cell is a human cell.

32. The method of claim 20, wherein about 20 to about 2000 placque forming units of adenovirus are present per eukaryotic cell to be contacted.

33. The method of claim 20, wherein said adenovirus is a wild-type strain.

34. The method of claim 20, wherein said adenovirus comprises genetic material with at least one modification therein.

35. The method of claim 34, wherein said modification renders said adenovirus replication-deficient.

36. The method of claim 34, wherein said modification is selected from the group consisting of addition of a DNA segment, rearrangement of a DNA segment, deletion of a DNA segment, replacement of a DNA segment, methylation of unmethylated DNA, demethylation of methylated DNA, and introduction of a DNA lesion.

37. The method of claim 34, wherein said modification alters the cell binding, endosomal lysis, or intracellular targeting capabilities of the adenovirus.

38. The method of claim 20, wherein said adenovirus comprises empty capsids.

39. The method of claim 20, wherein said adenovirus has been inactivated.

40. The method of claim 20, wherein said cationic agent is a polycarbene.

41. The method of claim 20, wherein said cationic agent is a liposome.

42. The method of claim 41, wherein said liposome is comprised of lipid.

43. The method of claim 20, wherein said cationic agent is a monocationic liposome.

44. The method of claim 43, wherein said monocationic liposome is comprised of lipid.

45. The method of claim 20, wherein said cationic agent is a polycationic liposome.

46. The method of claim 45, wherein said polycationic liposome is comprised of lipid.

47. The method of claim 45, wherein said polycationic liposome is comprised of dioctadecylamidoglycylspermine.

48. The method of claim 40, wherein said cationic agent is present in an amount sufficient for transfection in the absence of said adenovirus.

49. The method of claim 1, wherein said cell is contacted with said adenovirus simultaneously with said nucleic acid.

50. The method of claim 21, wherein said cell is contacted with said adenovirus simultaneously with said nucleic acid and said cationic agent.

* * * * *